US008768724B2

(12) United States Patent
Whiddon et al.

(10) Patent No.: US 8,768,724 B2
(45) Date of Patent: Jul. 1, 2014

(54) SYSTEM AND METHOD FOR DETECTING DRUG FRAUD AND ABUSE

(75) Inventors: Roger Whiddon, Simsbury, CT (US); Aneta Andros, Berlin, CT (US); Jeff Wasik, Unionville, CT (US); Michelle Sadak, Glastonbury, CT (US)

(73) Assignee: The Travelers Indemnity Company, Hartford, CT (US)

(*) Notice: Subject to any disclaimer, the term of this patent is extended or adjusted under 35 U.S.C. 154(b) by 60 days.

(21) Appl. No.: 13/095,145

(22) Filed: Apr. 27, 2011

(65) Prior Publication Data

US 2011/0288886 A1 Nov. 24, 2011

Related U.S. Application Data

(60) Provisional application No. 61/328,515, filed on Apr. 27, 2010.

(51) Int. Cl.
*G06Q 50/00* (2012.01)
(52) U.S. Cl.
USPC ............................................................ 705/2
(58) Field of Classification Search
USPC ...................................................... 705/2–3
See application file for complete search history.

(56) References Cited

U.S. PATENT DOCUMENTS

| 7,813,944 | B1 | 10/2010 | Luk et al. | |
|---|---|---|---|---|
| 2002/0032581 | A1* | 3/2002 | Reitberg | 705/2 |
| 2002/0143582 | A1 | 10/2002 | Neuman et al. | |
| 2004/0039257 | A1 | 2/2004 | Hickle | |
| 2009/0106313 | A1 | 4/2009 | Boldyga | |
| 2009/0138289 | A1 | 5/2009 | Klass et al. | |
| 2009/0216560 | A1* | 8/2009 | Siegel | 705/3 |

OTHER PUBLICATIONS

Simeone, Ronald, and Lynn Holland. "An evaluation of prescription drug monitoring programs." Retrieved Jan. 29 (2006): 2007.; http://pmpexcellence.org/pdfs/simeone_pdmp_eval2_2006.pdf.*
Schloff, Lisa A., et al. "Identifying controlled substance patterns of utilization requiring evaluation using administrative claims data." American Journal of Managed Care 10 (2004): 783-790. http://ehealthecon.hsinetwork.com/05_2004_AJMCO4nov_Parente783to90.pdf.*
International Search Report and Written Opinon of PCT/US2011/034120 dated Dec. 20, 2011.
International Search Report for PCT/US2011/034120 mailed Dec. 23, 2011, 3 pp.
International Written Opinion for PCT/US2011/034120 mailed Dec. 23, 2011, 5 pp.
International Preliminary Report on Patentability for PCT/US2011/034120 mailed Oct. 30, 2012, 6 pp.

* cited by examiner

*Primary Examiner* — Lena Najarian
*Assistant Examiner* — Minnah Seoh
(74) *Attorney, Agent, or Firm* — Fincham Downs LLC; Carson C. K. Fincham

(57) ABSTRACT

A system and method for detecting improper drug use utilizes the morphine equivalency of a drug regimen of a patient having an injury to compare the morphine equivalency of the drug regimen of the patient to that of a peer group having the same diagnosis. The comparison may be conducted based on the aggregate morphine equivalency for respective periods of time following the injury or the initial treatment and based on the rate of change in the morphine equivalency for that or another period of time. Based on the results of the comparison, potential instances of drug fraud and/or drug abuse are identified and an alert is generated, and appropriate action is taken, where needed.

31 Claims, 11 Drawing Sheets

PHARMACEUTICAL USE BY DOSAGE FOR FIRST FIVE WEEKS

AGGREGATION OF PHARMACEUTICAL USE BY DOSAGE FOR FIRST FIVE WEEKS

PHARMACEUTICAL USE BY MORPHINE EQUIVALENCY FOR FIRST FIVE WEEKS

AGGREGATION OF PHARMACEUTICAL USE BY MORPHINE EQUIVALENCY FOR FIRST FIVE WEEKS

AGGREGATION OF PHARMACEUTICAL USE BY MORPHINE EQUIVALENCY PER WEEK FOR TWENTY-SIX (26) WEEKS

RATE OF CHANGE OF AGGREGATION OF PHARMACEUTICAL USE

NOTICE OF FRAUD/ABUSE
DATE: _____ TIME: _____

PATIENT NAME: _____
PRESCRIBED DRUG: _____
PRESCRIBING DOCTOR: _____
PHARMACY: _____
DESCRIPTION OF FRAUD/ABUSE: _____
_____

PORTAL

*FIG. 14*

SYSTEM AND METHOD FOR DETECTING DRUG FRAUD AND ABUSE

CROSS-REFERENCE TO RELATED APPLICATIONS

The benefit of priority is claimed under 35 U.S.C. §119(e) of U.S. Provisional Patent Application No. 61/328,515 filed Apr. 27, 2010, and entitled "System and Method for Detecting Drug Fraud and Abuse," which is incorporated by reference herein in its entirety.

FIELD OF THE INVENTION

The present invention relates to a drug use detection system and method and, more specifically, to a system and method for analyzing medical data to detect drug fraud and/or drug abuse.

BACKGROUND OF THE INVENTION

The health care industry is a vast and complex enterprise in which significant advancements are being made at all levels. For example, medical knowledge and the quality of care provided to patients has improved, in part, through increased specialization of doctors. While such specialization has provided advantages to patients, it may also create drawbacks in the diagnosis and treatment of injuries. For example, a patient may need to see numerous doctors in order to address the complications that may result from a single injury or illness. This effect may be compounded where the patient suffers from numerous injuries or severe or complex illnesses.

In addition, medical treatment and pharmaceutical prescription options have improved such that there are numerous possible courses of treatment for any diagnosis or injury. As an example, a range of pain relievers, anti-inflammatory drugs, and other medications can be prescribed in response to a particular injury.

Also, based on external factors such as pricing discrepancies, insurance coverage limits for in-network versus out-of-network providers and/or the existence of multiple insurance programs, a patient may visit numerous different pharmacies to fill prescriptions that may have been issued by several different doctors.

As a result of the increased specialization of doctors, the availability of a wider scope of appropriate medications, and the greater administrative burdens associated with filling prescriptions at numerous pharmacies, medical billing records have consequently become more detailed and complex.

In some cases, such greater complexity has resulted in the potential for numerous problems in the provision of health care. In particular, doctors who make diagnostic and treatment decisions on behalf of a patient may not always have access to or knowledge of the patient's complete medical history. Additionally, even if the doctors do have access to the patient's entire medical history as of a particular time, information associated with a doctor's visit may be delayed before it is made accessible from a centralized repository, which may create opportunities for redundant or multiple treatments. As a result of such delays, doctors may improperly diagnose or treat a patient by over-treating a condition and/or issuing conflicting treatments.

Improper treatment also increases the cost of insurance claim payouts. For example, over-treatment or mistreatment directly increases the cost of medications for a given patient and may also result in side effects that can be as difficult and expensive to treat as the initial injury or ailment. In the aggregate, improper treatment may increase costs industry wide.

Improper treatment is a particular concern when a patient develops a dependency on or an addiction to a medication. Dependency and addiction can form if the patient is, for example, prescribed too large an amount of a medication before the patient's body has had time to develop a tolerance to the treatment. In addition, once a patient becomes dependent upon or addicted to a medication, the patient's primary treatment (i.e., for the initial injury or ailment for which the medication was first prescribed) must be adjusted to combat the dependency or addiction.

Although dependency and addiction are a concern for many categories of medications, the risks of dependency and addition are particularly pronounced for patients who are prescribed narcotics, i.e., drugs having morphine-like properties. Narcotics are highly addictive and patients who take narcotics run a high risk of becoming dependent on those medications. Once a dependency or an addiction to a particular drug forms, patients are often switched to a different drug, i.e., an opioid such as methadone, in order to maintain the requisite pain relieving effect but with a more manageable risk of dependency. However, the use of methadone has its own risks of dependency. For example, in 2004, methadone abuse contributed to the death of approximately 4,000 individuals in the United States alone, an increase of approximately 400% since 1999.

In addition to the immediate risk to the health of patients, the costs of providing health care to patients who become addicted to or otherwise abuse narcotics are, on average, approximately eight times greater than the costs of providing health care to non-abusers. Ideally, the preemptive detection of dependency or addiction would provide the patient with treatment options that could mitigate or combat the dependency or addiction early on, when treatment would be most effective. However, preemptive detection of the dependency or addiction may be difficult, depending on the nature of the patient's injury, the number of doctors who provide treatment to the patient, or the complexity of the patient's drug regimen. In addition, lack of access to the patient's full medical history, as discussed above, further compounds the problem of early detection.

Another problem accentuated by the increased size and complexity of the health care industry is fraud, such as insurance billing abuse, illegitimate billing practices, and drug diversion, e.g., the use of prescription drugs for recreational purposes. Drug diversion alone cost the United States insurance industry an estimated $72.5 billion in 2008 and is particularly significant because it poses a public health and safety risk as medications are made available through the black market. In these unregulated channels, drug abuse proliferates.

BRIEF DESCRIPTION OF THE DRAWINGS

The illustrated embodiments of the system and method of the present invention are intended to illustrate, but not limit, the invention.

FIG. 14 depicts an example notice of fraud or abuse according to an embodiment of the present invention.

DETAILED DESCRIPTION OF THE PREFERRED EMBODIMENTS

Figure 1:
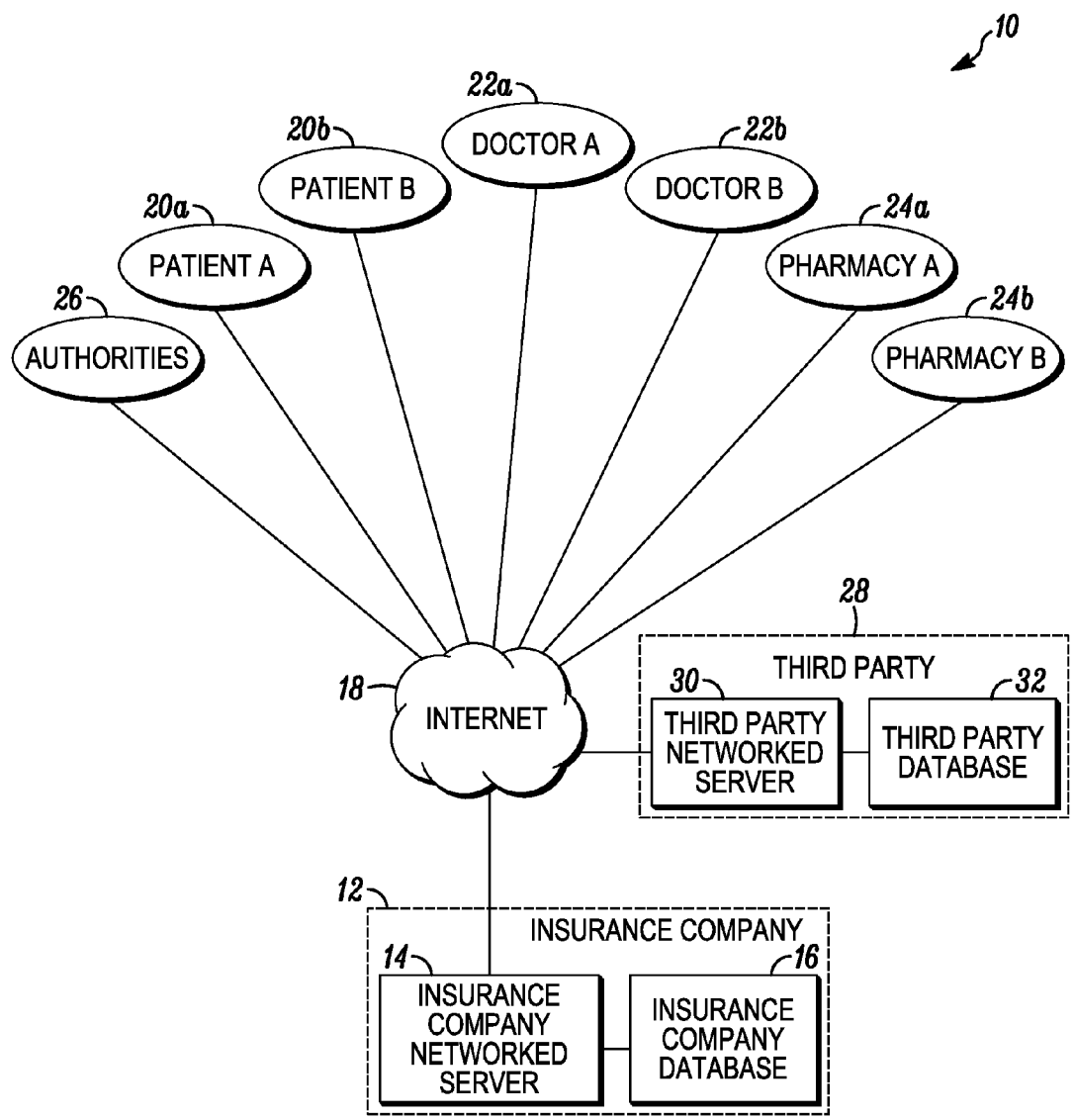
FIG. 1 is a diagram of a communications network according to an embodiment of the present invention.

Referring to FIG. 1, a systems-level review of a network including a system according to an embodiment of the present invention is shown. In particular, FIG. 1 shows a system 10 connected to an insurance company 12, having a networked server 14 and one or more databases 16, and to a number of other parties over a network 18, such as the Internet or other communications network. More specifically, the insurance company 12 may be connected to computer terminals associated with patients 20a, 20b, doctors 22a, 22b, pharmacies 24a, 24b and one or more relevant authorities 26, which may include support groups, a professional ethics or grievance committee, state or local police, and/or the federal Drug Enforcement Agency ("DEA"), for example.

The insurance company 12 may also be connected via the Internet 18 to a third party 28, having a third party networked server 30 and a third party database 32. The third party 28 may supply information or data that may be useful throughout the insurance claim handling process. For example, the third party 28 may provide access to additional data and known or proprietary services, processing techniques, or algorithms for tracking, analyzing or assessing treatments, such as prescriptions of drugs or drug regimens. Other arrangements of hardware, including various networked client and server computers, may also be used by the insurance company 12 and the third party 28.

Those of skill in the pertinent art will recognize that the one or more insurance companies 12, patients 20a, 20b, doctors 22a, 22b, pharmacies 24a, 24b, authorities 26 and third parties 28 may use a keyboard, keypad, mouse, stylist, touch screen, "smart" phone or other device (not shown) or method using a browser or other like application for interacting with an external network, such as the Internet 18. The computers, servers, and the like described herein have the necessary electronics, software, memory, storage, databases, firmware, logic/state machines, microprocessors, communication links, displays or other visual or audio user interfaces, printing devices, and any other input/output interfaces to perform the functions described herein and/or achieve the results described herein.

Except where otherwise explicitly or implicitly indicated herein, the terms "patient," "doctor," "pharmacy," "authorities," "insurance company" or "third party" also refer to the associated computer systems operated or controlled by a patient, doctor, pharmacy, authority, insurance company or third party, respectively. Furthermore, those of skill in the art will also recognize that process steps described herein as being performed by a "patient," "doctor," "pharmacy," "authorities," "insurance company" or "third party" may be automated steps performed by their respective computer systems, and may be implemented within software modules (or computer programs) executed by one or more general purpose computers.

The protocols and components for providing the respective communications between the insurance company 12, the patients 20a, 20b, the doctors 22a, 22b, the pharmacies 24a, 24b, the third parties 28 and the Internet 18 are well known to those skilled in the art of computer communications. As such, they need not be described in more detail herein. Moreover, the data and/or computer executable instructions, programs, firmware, software and the like (also referred to herein as "computer executable components") described herein may be stored on a computer-readable medium that is within or accessible by computers or servers and may have sequences of instructions which, when executed by a processor (such as a central processing unit, or CPU), may cause the processor to perform all or a portion of the functions and/or methods described herein. Such computer executable instructions, programs, software and the like may be loaded into the memories of computers or servers, using drive mechanisms associated with the computer readable medium, such as a floppy drive, CD-ROM drive, DVD-ROM drive, network interface, or the like, or via external connections.

Figure 2:
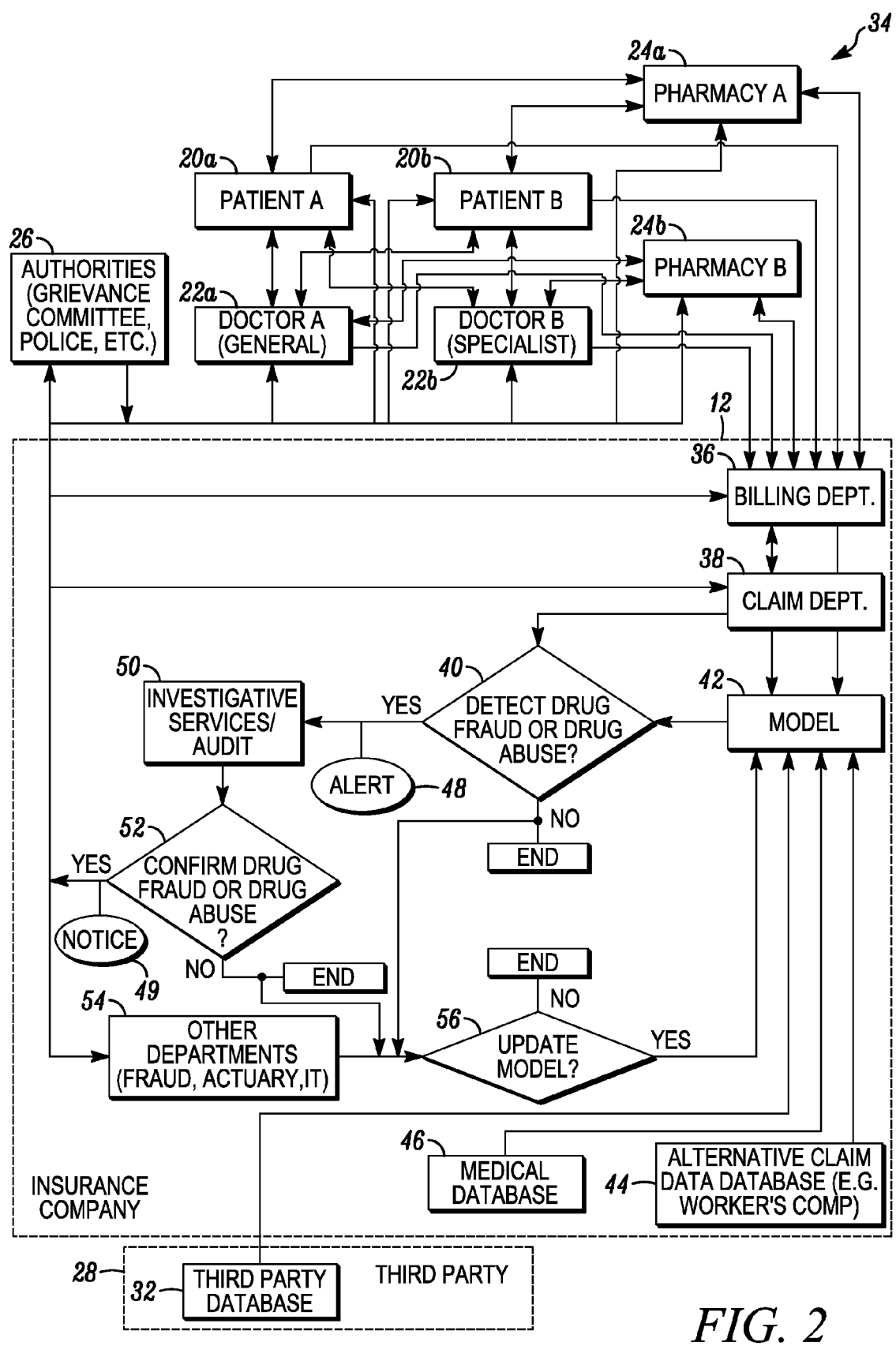
FIG. 2 is a flow diagram of an insurance relationship according to an embodiment of the present invention.

Referring to FIG. 2, a diagram of an insurance relationship 34 conducted using the system 10 is shown. It should be appreciated that communications between the various parties shown in FIG. 2 may be provided by any means, such as electronic exchanges, electronic mail and short message service, wireless communication, as well as telephone calls and regular mail, without departing from the present invention. The system and method of the present invention may be used within health insurance and/or property/casualty insurance, including, for example, worker's compensation, first party medical (i.e., auto, property or general liability), and/or third party medical (i.e., auto, property or general liability), but may also apply to any other areas of insurance or other industries where a company or individual has an interest in determining drug/medication fraud and/or abuse (including, for example, dependence, addiction, billing abuse, and diversion), such as that described herein or otherwise. The term "improper drug use" is used synonymously herein with drug fraud and drug abuse.

As illustrated in FIG. 2, a number of the patients 20a, 20b (collectively 20) may hold insurance policies with the insurance company 12. When a patient 20 suffers an ailment or injury (hereinafter "injury"), the patient 20 may visit one or more doctors 22, including a general practice doctor 22a (e.g., primary care physicians) or a specialist doctor 22b (e.g., surgeons and anesthesiologists), respectively, to receive treatment for the injury. The doctors 22 can, as one course of action, issue prescriptions for a prescription drug regimen to the patient 20 to address the injury. The drug regimen may comprise a prescription of at least one drug for consumption by the patient. As used herein, "consumption" of a drug includes eating, drinking, injecting, smoking, inhaling, absorption through a patch or otherwise, and other ingestion methods.

The patient 20 may fill the prescription either by receiving medications associated with the prescription drug regimen from the doctor 22 directly or by visiting one or more pharmacies 24a, 24b (collectively 24). In the ordinary course of business, each patient 20 may see a number of doctors 22 at any point in time, each doctor 22 will, in turn, see a number of patients 20, and each patient 20 and doctor 22 may have a relationship with a number of the pharmacies 24.

Following a visit of the patient 20 to the doctors 22, any associated medical bills, including insurance claims, may be generated by the doctors 22 or the pharmacies 24, and supplemented by the patients 20. The medical bills may be sent to a billing department 36 of the insurance company 12, which may perform the initial processing of the claims for completeness and formatting issues.

Once processed, the claims are forwarded to a claim department 38 of the insurance company 12. The claim department 38 performs a preliminary substantive review, which may involve, at box 40, an analysis of the claims using one or more drug fraud and drug abuse detection models 42 (see, e.g., FIGS. 10-12). The models 42 may be stored in a database 16 of the insurance company 12 and executed across the networked server 14 of the insurance company, and may be utilized to detect drug fraud and/or drug abuse and may issue an alert or flag if a possible instance of drug fraud or drug abuse is detected. In addition, the models 42 may receive data from a number of sources, including the billing department 36 and the claim department 38, as well as an alternative claim data database 44 (e.g., a worker's compensation claim database), a medical database 46 (e.g., a database of medical knowledge and statistics) or other databases, such as the third party database 32.

If no possible instance of drug fraud or drug abuse is detected, the process is ended. In some cases, the data associated with the preliminary substantive review may be provided to update, at box 56, the model 42, as needed.

If a possible instance of improper drug use (e.g., drug fraud or drug abuse) is detected by the model 42, an alert 48 may be generated and delivered via electronic mail, short message service (SMS) text message, multimedia message service (MMS) text message, or any other form of electronic or optical communication. Generating the alert 48 may include flagging and transmitting the claim to an investigative services or audit department 50 of the insurance company 12, which may review the claim more closely to determine or confirm, at box 52, the underlying circumstances or reasons the claim was flagged, and whether drug fraud or drug abuse is occurring.

In one embodiment, the alert 48 may be transmitted to entities within the insurance company 12 other than the investigative services or audit department 50, including the billing department 36, the claim department 38, and/or other departments, as well as entities outside the insurance company 12, such as one or more authorities 26, doctors 22, pharmacies 24, and/or other entities. The alert 48 in this embodiment may have an abbreviated form containing basic information identifying the possible instance of improper drug use. In some embodiments, in addition to or instead of the alert 48, a notice 49 (as described hereinafter) may be provided to the entities/areas as described herein for the notice 49.

If there is a reason or explanation as to why the claim was flagged, such as a subsequent compounding injury, the investigative services or audit department 50 may record a comment in a claim history file (not shown) and close the claim review process. The data associated with the analysis by the investigative services or audit department 50 may be provided to update, at box 56, the model 42, as needed. Refinements of the model 42 may reduce the occurrence of subsequent false positive detections of improper drug use.

If, however, there are indications of possible drug fraud or drug abuse (i.e., a YES at box 52), the investigative services or audit department 50 may follow up with appropriate actions, such as by issuing further alerts or providing feedback to interested parties. In such cases, according to one embodiment, the investigative services or audit department 50 transmits a notice of fraud/abuse 49 to entities within the insurance company 12, including the billing department 36, the claim department 38, and other departments, as well as entities outside the insurance company 12, such as one or more authorities 26, doctors 22, pharmacies 24, and/or other entities. Such notices 49 may be transmitted via electronic mail, short message service (SMS) text message, multimedia message service (MMS) text message, or any other form of electronic or optical communication. An example notice of fraud/abuse 49 is shown in FIG. 14. In the illustrated embodiment, a link is provided, such as a URL (identified as "PORTAL" in FIG. 14), that allows a recipient of the notice 49 to connect to an alert display 153, discussed below with regard to FIG. 13. In some embodiments, in addition to or instead of the notice 49, the alert 48 (as described herein) may be provided to the entities/areas as described herein for the alert 48.

As an initial response to a legitimate alert 48, for example, the investigative services or audit department 50 may inform the claim department 38 and the billing department 36 of the possible drug fraud or drug abuse in order for the claim department 38 or the billing department 36 to deny or modify coverage or to work with doctors to modify treatment.

The investigative services or audit department 50 may also inform other departments 54 of the insurance company 12, such as a fraud analytics, actuarial, or information technology department. The other departments 54 may use knowledge of identified instances of drug fraud or drug abuse to update, at box 56, the model 42 as needed. The process of updating the model 42 may include augmenting the data imported from the billing department 36 and the claim department 38 to account for identified instances of drug fraud and/or drug abuse, and may be performed automatically or manually. The process of updating the model 42 may also include revising existing patterns that identify drug fraud and/or drug abuse, or calculating additional patterns that identify drug fraud and/or drug abuse, such as by using statistical techniques, including outlier, regressions, and/or neural network analyses.

The investigative services or audit department 50 may also take action outside of the insurance company 12, as needed. For example, the department 50 may contact a number of the authorities 26 and, either alone or in conjunction with the authorities 26, may also contact the patient 20, the doctor 22, and/or the pharmacy 24 involved with the claim that has been identified as an instance of drug fraud and drug abuse. In the case of an identified instance of drug dependency or addiction, the patient 20, the doctor 22, and/or the pharmacy 24 may update the treatment of the patient 20 to mitigate or reverse the formation of the drug dependency or addiction. In the case of an identified instance of drug billing abuse or diversion, the authorities 26 can pursue the responsible patient 20, doctor 22, and/or pharmacy 24 to address the fraud.

In a system and method in accordance with one embodiment of the present invention, the model 42 may provide a comparison of disparate medications according to a standardized morphine equivalency and, thus, may have particular applicability to narcotics. However, the system and method of the present invention may also be applied to other types of medications that can be standardized to another equivalency.

Figure 3:
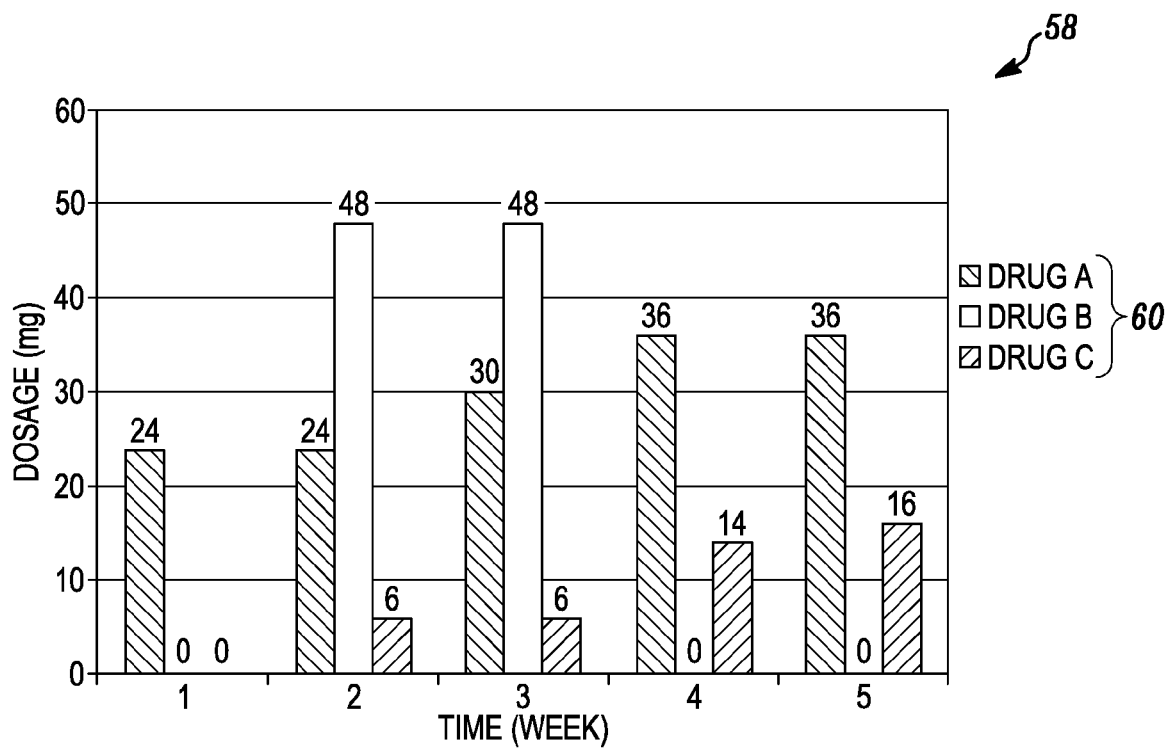
FIG. 3 is a bar graph of a prescription drug regimen of a patient showing the dosage of each medication taken over a period of five weeks and illustrative of an embodiment of the present invention.

Referring to FIG. 3, an exemplary bar graph 58 of a prescription drug regimen 60 of a patient is shown. The bar graph 58 illustrates the dosage (by weight, such as 100 mg per unit of dosage) of three drugs—Drug A, Drug B and Drug C—that the patient is prescribed during each of the first five weeks after sustaining the injury and/or receiving treatment. As shown in Table 1, below, the patient is prescribed the following amount of each of the three drugs:

TABLE 1

Prescription Drug Regimen Dosage Amount by Week

| Week | Drug A | Drug B | Drug C | TOTAL |
| --- | --- | --- | --- | --- |
| 1 | 24 | 0 | 0 | 24 |
| 2 | 24 | 48 | 6 | 78 |
| 3 | 30 | 48 | 6 | 84 |
| 4 | 36 | 0 | 14 | 50 |
| 5 | 36 | 0 | 16 | 52 |

Figure 4:
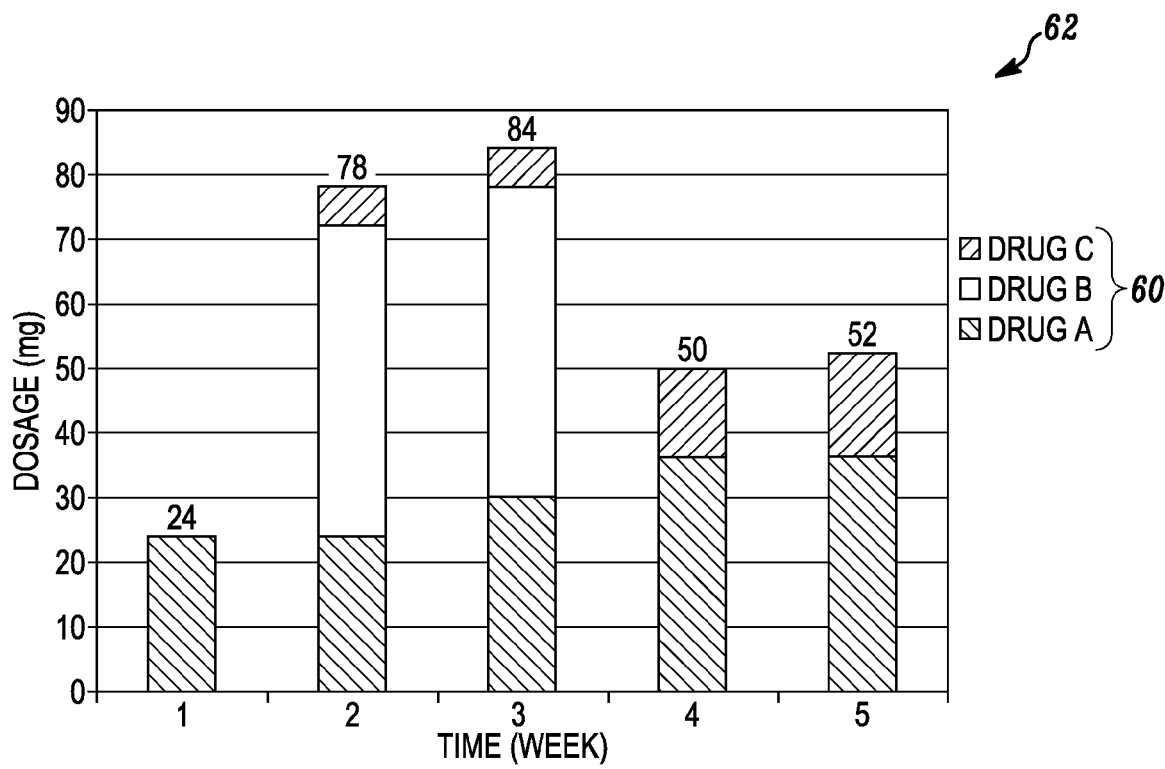
FIG. 4 is a stacked bar graph of the prescription drug regimen of FIG. 3.

Referring to FIG. 4, a stacked bar graph 62 illustrates the drug regimen information shown in Table 1 and in FIG. 3, aggregated by week. From the drug regimen data shown in Table 1 and represented in the accompanying FIGS. 3 and 4, it can be determined that the patient 20 has increased the use of Drug A, tried Drug B briefly, and started using Drug C. However, the actual implications of the prescription drug regimen 60 may not be readily apparent from Table 1 or from FIG. 3 or FIG. 4. For example, it is possible that the patient may have developed a dependency on one or more of these medications that would not be readily discernable by simply reviewing the data presented in Table 1, FIG. 3 or FIG. 4.

According to embodiments of the present invention, a prescription drug regimen 60 may be standardized to a morphine equivalency scale to allow the detection of drug fraud and drug abuse. In one embodiment, the morphine equivalency of each medication may be computed according to the following equation:

$$\text{Morphine Equivalency} = \text{Calculated Daily Dosage} * \text{Morphine Equivalency Coefficient} \qquad \text{Equation 1}$$

The Calculated Daily Dosage of the medication is a measurement of the amount of the medication, such as the values listed in Table 1, which is being taken by the patient 20 on a daily basis, or per another unit of time. Depending on the information presented in the medical billing data, it may be necessary to compute the Calculated Daily Dosage by dividing the total prescribed amount of narcotics (e.g., 480 mg) by the usage period (e.g., 30 days) or, alternatively, by multiplying the dosage of each pill (e.g., 10 mg/pill) by the number of pills that are to be taken each day (e.g., 4 pills/day) to arrive at a value expressed in quantity per day (e.g., mg/day). The Morphine Equivalency Coefficient of the medication is a coefficient that relates the potency of the medication to that of morphine (e.g., 100 mg of morphine/100 mg of medication prescribed, measured in "units"). The Morphine Equivalency Coefficient may be determined based on known scientific or medical data, which may be stored, for example, in the medical database 46 shown in FIG. 2.

Figure 5:
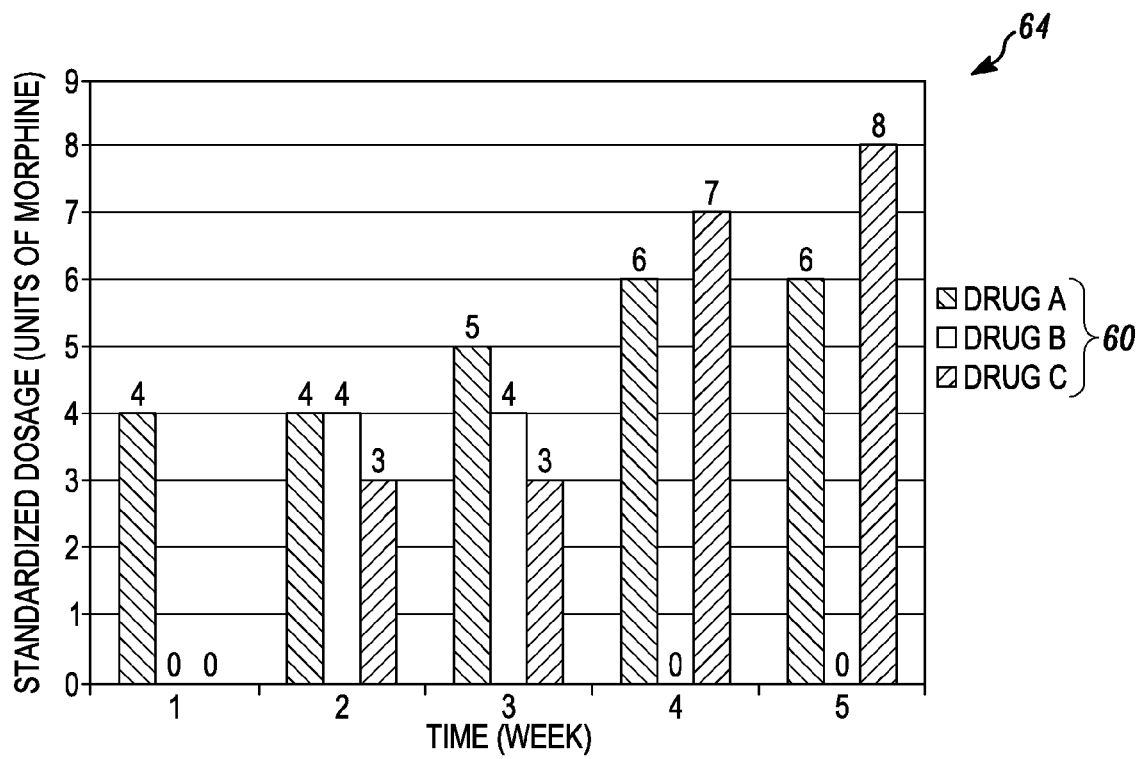
FIG. 5 is a bar graph of the morphine equivalency of the prescription drug regimen of FIG. 3.

Referring to FIG. 5, a bar graph 64 of the Morphine Equivalency of each medication of the prescription drug regimen 60 is shown. The quantities are shown in units of morphine. For example, the Calculated Daily Dosage of 24 mg of Drug A that was taken in week 1, as is shown in Table 1 and in FIG. 3, is shown as having a Morphine Equivalency of 4 units morphine in FIG. 5. Therefore, it can be inferred that Drug A has a Morphine Equivalency Coefficient of 4 units morphine/24 mg, or ⅙ unit morphine/mg. Similarly, the Calculated Daily Dosages of 48 mg of Drug B and 6 mg of Drug C that were taken in week 2, as is shown in Table 1 and in FIG. 3, are shown as having Morphine Equivalencies of 4 units morphine and 3 units morphine, respectively, in FIG. 5. Therefore, it can be inferred that Drug B has a Morphine Equivalency Coefficient of 4 units morphine/8 mg, or ¹⁄₁₂ unit morphine/mg, and that Drug C has a Morphine Equivalency Coefficient of 3 units morphine/6 mg, or ½ unit morphine/mg.

Figure 6:
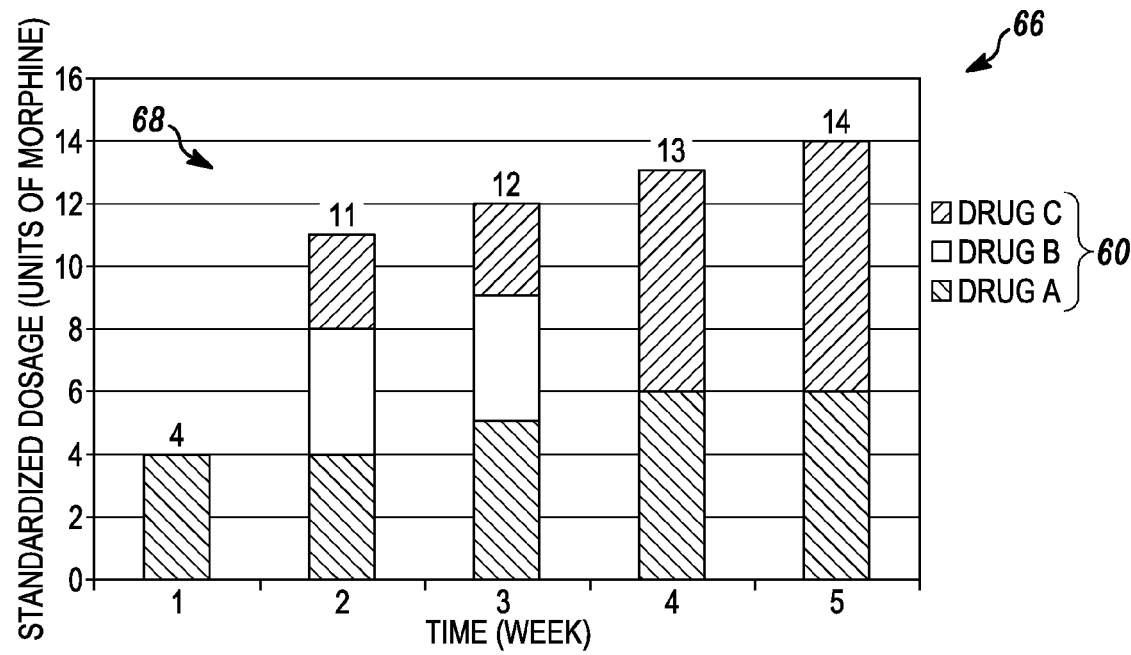
FIG. 6 is a stacked bar graph of the morphine equivalency of the prescription drug regimen of FIG. 5.

Referring to FIG. 6, a stacked bar graph 66 illustrates the morphine equivalency data shown in FIG. 5, aggregated by week. Based on the weekly aggregate 68 of the prescription drug regimen 60 of the patient 20 shown in FIG. 6, it is apparent that the patient is increasing his or her overall intake of morphine equivalency from week to week. In addition, the percentage of the total prescription drug regimen 60 that each drug comprises from a functional (i.e., effect on the body), rather than raw dosage, perspective is more readily apparent. Such information, which may not be evident from FIG. 3 or FIG. 4, explains how dependency, addiction, billing abuse, and diversion could avoid detection if the wrong data is reviewed, or if accurate data is not reviewed in connection with all other relevant treatment data.

Figure 7:
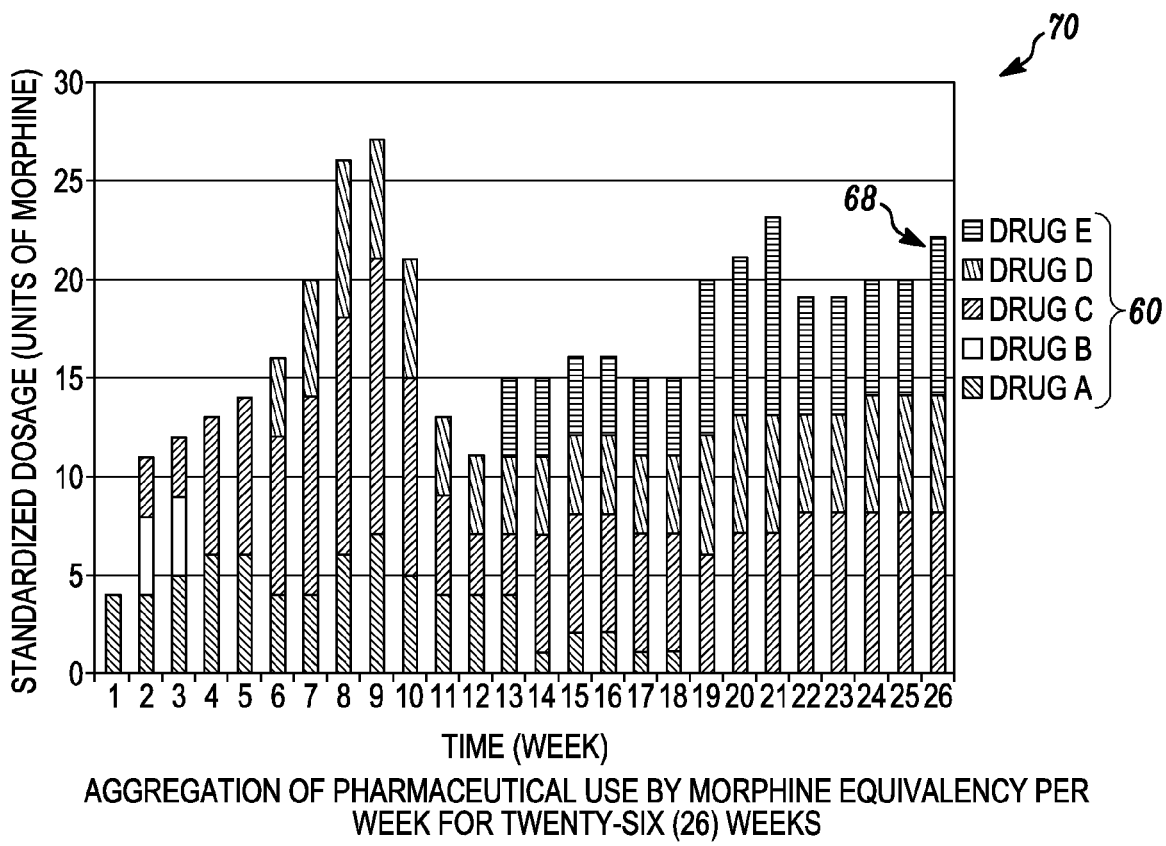
FIG. 7 is a stacked bar graph of the morphine equivalency of a prescription drug regimen of FIGS. 3-6 expanded for a period of 26 weeks.

Referring now to FIG. 7, morphine equivalency data of the patient's prescription drug regimen 60 over a 26-week period of time is illustrated as a stacked bar graph 70. FIG. 7 once again shows that morphine equivalency of the aggregate 68 of the prescription drug regimen 60 increases over a period of time. The first five weeks are the same as shown in FIG. 6. FIG. 7 also shows the impact of additional medications, such as Drug D and Drug E, that may be added to the prescription drug regimen 60 over time.

Figure 8:
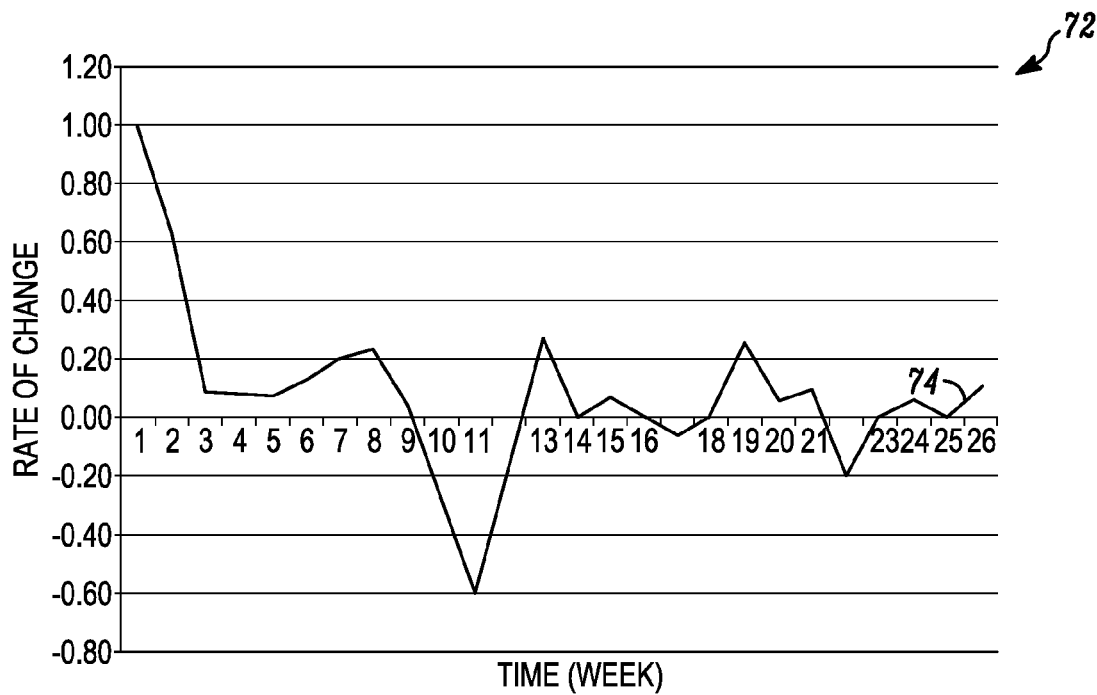
FIG. 8 is a line graph of the rate of change of the morphine equivalency of the prescription drug regimen of FIG. 7.

Some embodiments of the present invention include examining the rate of change of pharmaceutical use to provide useful information for detecting drug fraud and/or abuse by comparing the morphine equivalency of a drug regimen at one time to the morphine equivalency of the drug regimen at a previous time. Referring now to FIG. 8, a graph 72 illustrating the average daily rate of change (or ROC) 74 of morphine equivalency of the prescription drug regimen 60 over the 26-week period represented in FIG. 7 is shown. The rate of change 74 shown in FIG. 8 may be calculated using the following equation:

$$\text{ROC} = ((\text{Amount}_T - \text{Amount}_{T-1}) / (\text{Amount}_{T-1})) \qquad \text{Equation 2}$$

where $\text{Amount}_T$ and $\text{Amount}_{T-1}$ are morphine equivalencies at time T and time T−1, respectively.

As shown in FIG. 8, the patient experiences a rapid increase in the amount of morphine equivalency of the prescription drug regimen 60 during the first few weeks of treatment, followed by a sustained positive increase as the patient 20 adjusts to the prescription drug regimen 60 and the pain of the injury. As the patient 20 recovers, the amount of medication can be reduced. However, over time, the patient 20 may experience an increased tolerance or resiliency to the medication and a relatively slow increase in the morphine equivalency of the prescription drug regimen 60. More significant increases of the tolerance or resilience of the patient 20 to the medication, expressed as increases in the rate of change 74 of morphine equivalency of the prescription drug regimen 60, may provide an indication of a possible drug dependency or addiction.

Figure 9:
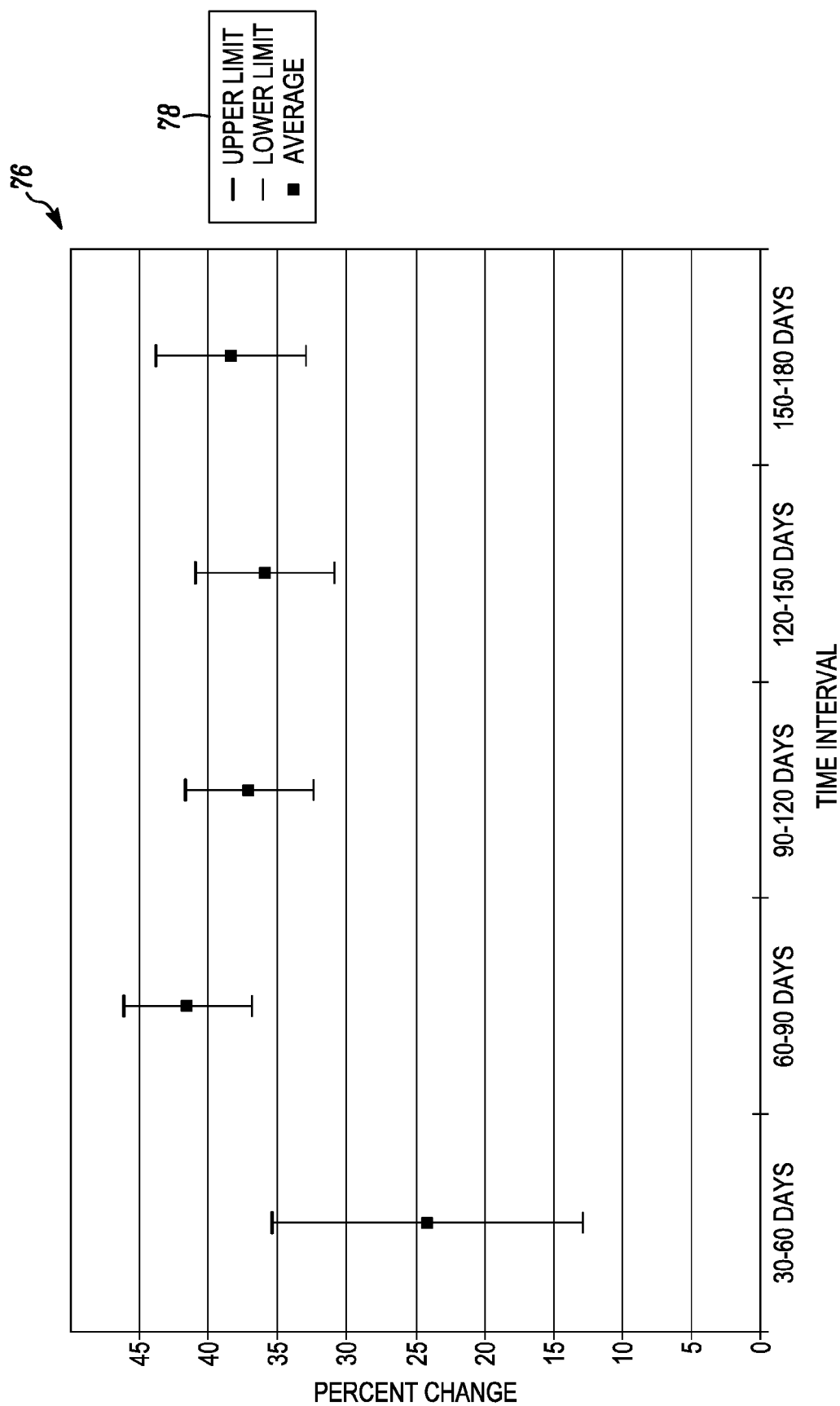
FIG. 9 is a line graph of a prescription drug regimen of a peer group with confidence intervals over 180 days.

Referring to FIG. 9, a graph 76 of the rate of change of morphine equivalency of a prescription drug regimen 78 of a primary diagnosis group, e.g., a peer group of patients, is shown. The graph 76 illustrates confidence intervals, set at three standard deviations (3σ) from an average value of the prescription drug regimen 78 of the peer group for each month over an extended period of time, namely, from 30 days through 180 days, or approximately 26 weeks, after the injury or the initial treatment.

As will be appreciated with reference to FIGS. 3-9, the human body develops a tolerance or resiliency to the effects of the medications over time. This is generally true independent of factors such as prior medical history (e.g., prior or recent use of narcotics), the injury sustained, and other attributes of the patient (e.g., patient demographic information, such as gender, age, height, weight, genetic markers, or indicators of drug metabolism rate, as well as the cross-effect of other medications or other disorders and diseases, comorbidity factors, etc.). However, by taking these and other factors into consideration, the aggregate 68 amount of morphine equivalency and rate of change 74 of the prescription drug regimen 60 can be normalized for a sample set of patients (i.e., the peer group) having a given set of such factors to ascertain additional meaning from the data. For example, to ascertain additional meaning from the data, the following process may be employed in accordance with some embodiments of the present invention.

Figure 10:
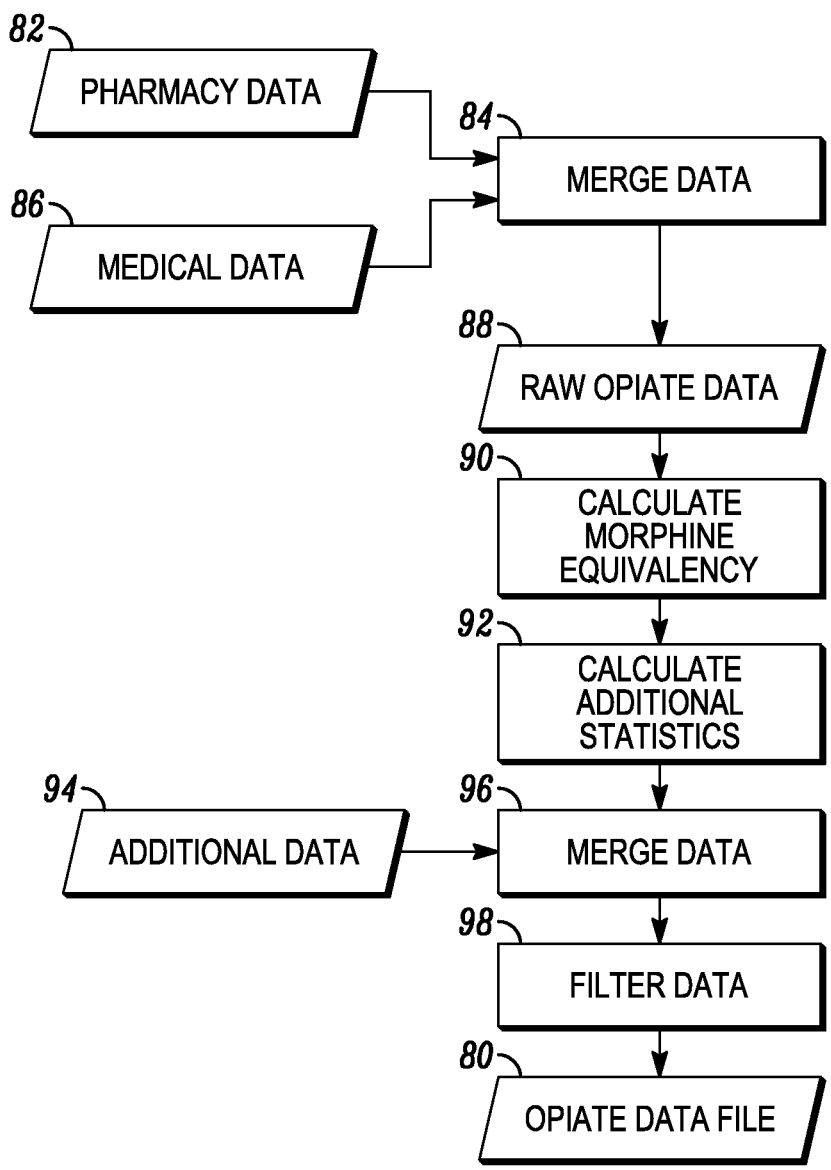
FIG. 10 is a flow diagram of the data acquisition and pre-processing of medical billing records of the system and method according to an embodiment the present invention.

Referring to FIG. 10, a flow chart for preparing an opiate data file is shown. First, data may be initially gathered from a variety of sources and processed to form the opiate data file 80, which comprises the working data set for the detection model 42. Pharmacy data 82 from one or more pharmacies 24, doctors 22 and/or patients 20 may be gathered by the billing department 36 of the insurance company 12, or, depending on the type of insurance (i.e., worker's compensation insurance rather than health insurance), from a third party medical billing specialist, such as HealthE, for example. The pharmacy data 82 may include date information that may be used to synchronize and chronologically organize one or more prescriptions issued for the patients 20. The pharmacy data 82 also may include data associated with the prescriptions, such as the National Drug Code ("NDC") of each medication prescribed and the dosage of each medication. A complete list of NDCs is maintained and accessible on the Food and Drug Administration ("FDA") website.

An exemplary list of common narcotics includes: codeine, fentanyl, hydrocodone, hydromorphone, levorphanol, meperidine, methadone, morphine, opium, oxycodone, and propoxyphene. A complete list of narcotics is maintained and accessible on the Drug Enforcement Agency ("DEA") website.

At box 84, the pharmacy data 82 may be merged with medical data 86 to generate raw opiate data 88. The medical data 86 may be stored in the medical database 46 and may include data relating to the morphine equivalency coefficients of individual narcotic medications.

Next, at box 90, the morphine equivalency of the prescription drug regimen may be calculated based on the raw opiate data 88 per prescription period. The morphine equivalency may be calculated by cross-referencing the NDC of each medication in the prescription drug regimen 60 of each prescription with a morphine equivalency of the medication, which may be stored in the medical database 46, and by multiplying the cross-referenced morphine equivalency by the dose of each medication, in accordance with Equation 1.

The morphine equivalency may be calculated on a daily basis to analyze the prescription drug regimen, as evidenced by the prescription issuance and fulfillment history, over the likely period of actual use. If the pharmacy data 82 or the medical data 86 includes information about a ramping dosage instruction, the ramping dosage instruction can be used to define the likely period of use. However, in the absence of specific indications, the daily morphine equivalency may be calculated using an average of the total morphine equivalency of the prescription divided by the identified period of its use.

At box 92, the raw opiate data 88, morphine equivalency data and daily dose information is then used to calculate additional statistics and the date ranges of medication usage. For example, the morphine equivalency data in the raw opiate file 88 may be reviewed based on the timeliness and regularity of the issuance and the filling of prescriptions in order to quantify periods of under- or over-treatment based on the availability of the prescription drug regimen 60. In addition, the morphine equivalency data in the raw opiate file 88 may be used to determine a duration of medication usage. The duration may be calculated for the current injury, as well as for other injuries on record, and for each prescription issued by the doctors 22 and filled by the pharmacies 24.

At box 96, additional data 94 may be merged with the raw opiate data 88. The additional data 94 may include worker's compensation claims data or other claimant data derived from sources, such as the alternative claim data database 44. The additional data 94 may also include data received from the third party database 32, which may include, as discussed above, additional data and known or proprietary services, processing, and algorithms.

As a final step of the data gathering, at box 98, the raw opiate data 88 as adjusted, calculated, and merged may be filtered to exclude certain kinds of data or factors, such as particular injuries indicated in the claimant data that may disrupt the results of subsequent detection and analysis. For example, patients 20 who suffer from burns and brain injuries often exhibit erratic and extremely-high narcotics use due to the volatile effects of burns and brain injuries on the nervous system of the patient. As a result, without a sufficiently large data set and, in particular, a coding system that quantifies the severity of the burns and brain injuries, it may be difficult to analyze the raw opiate data 88 effectively and in a meaningful manner. Therefore, unless a sufficiently ample data set is generated, these kinds of factors may be excluded from the raw opiate data 88.

Once these data gathering and processing steps are complete, the resultant opiate data file 80 is ready for analysis by an embodiment of the systems and methods of the present invention.

It should be appreciated that the steps of the illustrated embodiments of the present invention may be performed in any order. For example, referring to the flow chart shown in FIG. 10, the data gathering and processing actions performed at boxes 90, 92, 96 and 98 may be readily reordered.

Figure 11:
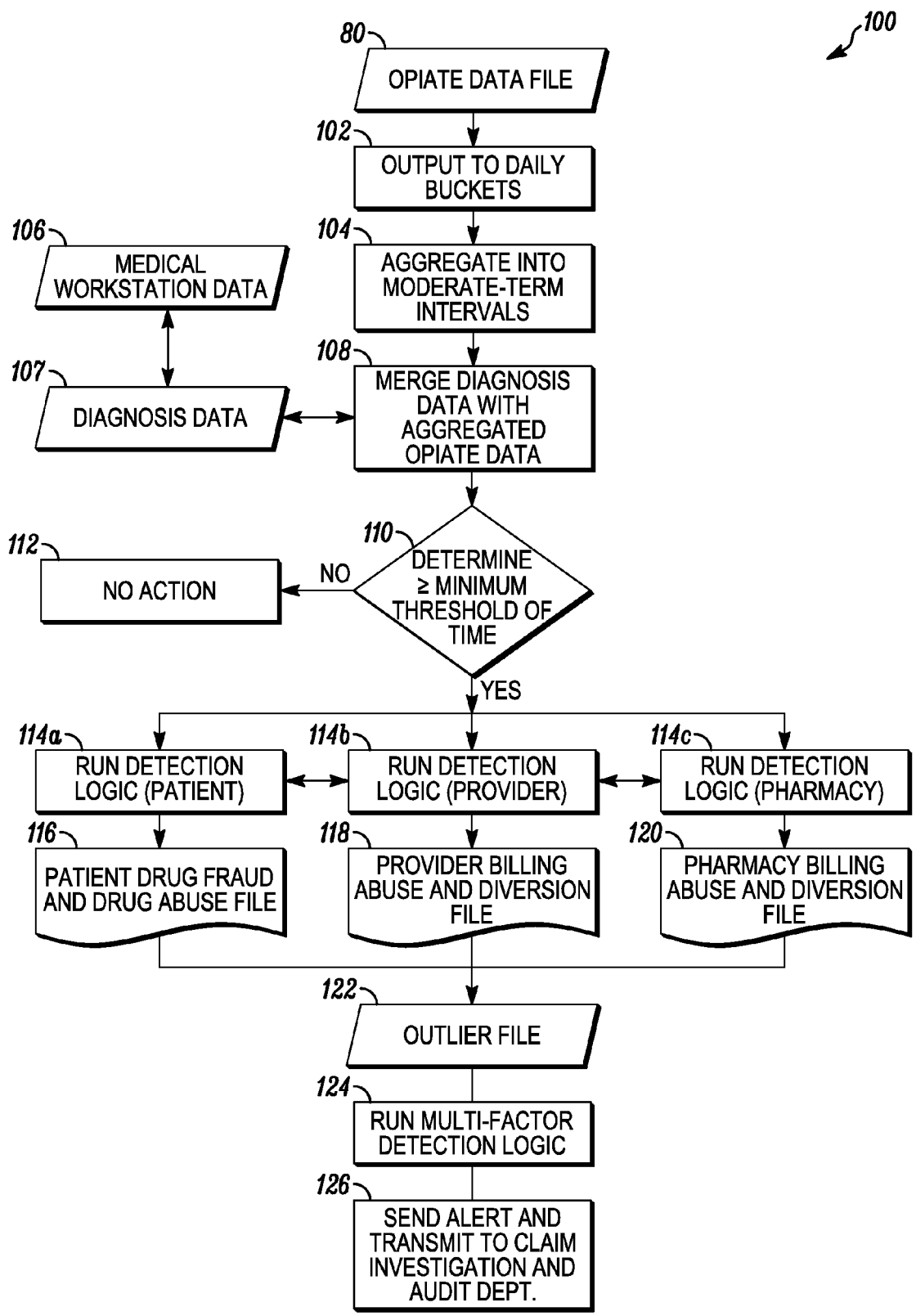
FIG. 11 is a flow diagram of an aggregation analysis model of the system and method according to an embodiment of the present invention.

Referring now to FIG. 11, an embodiment of an aggregate morphine equivalency analysis model 100 for analyzing an opiate data file 80 is shown. At box 102, the opiate data file 80 is first outputted into daily buckets of a calendar. The daily buckets may summarize the morphine equivalencies of a prescription drug regimen 60 of a patient 20 for each day.

At box 104, the daily buckets may then be aggregated into a number of moderate-term intervals, such as a 30-day period.

At box 108, diagnosis data 107 derived from medical workstation data 106, which may be typically stored by the claims department 38, is merged into the aggregated opiate data. In particular, the diagnosis data may include primary diagnosis indicators, and the medical workstation data 106 may include medical records provided by the doctors 22. The morphine equivalency of the prescription drug regimen 60 of the patient 20 is associated with the diagnosis data to establish a primary peer group against which the patient may be compared. The primary diagnosis indicators can be determined, for example, based on International Classification of Diseases ("ICD") codes that may be provided with the diagnosis data. ICD codes are maintained by the National Center for Health Statistics ("NCHS") and the Centers for Medicare & Medicaid Services ("CMS").

In one embodiment, a patient peer group comprises patients having the same ICD code, which indicates that those patients have the same diagnosis. In other embodiments, a peer group may comprise patients having the same injury or injuries or patients having one or more injuries resulting in a substantially similar aggregated effect.

Next, at box 110, it is determined whether the patient 20 has been on the prescription drug regimen 60 for more than a minimum threshold of time, such as 30 days of treatment. If the patient 20 does not have a treatment history that extends beyond the minimum threshold of time, then, at box 112, no further action is taken.

However, if the patient 20 has been on the prescription drug regimen 60 for more than the minimum threshold of time, a detection logic 114 is run on the treatment history and prescription drug regimen 60 at boxes 114a, 114b, 114c based on three views: a patient view (box 114a), a doctor view (box 114b) and a pharmacist view (box 114c). The detection logic 114 may be, for example, an outlier detection algorithm that compares data from the aggregated intervals of the patient 20, doctor 22, or pharmacy 24 to data from the aggregated intervals of a peer group of the patient 20, doctor 22, or pharmacy 24, respectively, on a per interval basis. In one embodiment, a peer group of doctors may comprise doctors having a similar specialty and/or doctors treating patients having similar types of injuries. Moreover, a peer group of pharmacies may comprise pharmacies distributing a comparable volume of prescriptions over a given period of time.

In the example of the model shown in FIG. 11, by running the detection logic 114 based on three views, three subfiles are generated including: a patient drug fraud and drug abuse file 116, a provider billing abuse and diversion file 118, and a pharmacy billing abuse and diversion file 120. The subfiles are configured for use within the three views, respectively, that are specific to each likely actor of an identified possible instance of drug fraud or drug abuse.

Once the subfiles 116, 118, 120 are generated, the subfiles 116, 118, 120 may be exported together as an outlier file 122. Next, a multi-factor detection logic 124 is run to analyze the outlier file 122 to detect whether a possible instance of an improper drug use has occurred.

In one embodiment, using the outlier file 122, the multi-factor (or multi-parameter or multi-indicator) detection logic 124 may be run in conjunction with other detection logic and data sets, to produce synergistic detection effects with each of the three views. The synergy of the multi-factorial detection logic 124 may result, in part, from the tendency of individuals, including patients, providers, and pharmacies, who commit at least one act of fraud to commit other acts of fraud, as well. Therefore, by looking at multiple indicators of fraud from each of the three views, the overall accuracy and sensitivity of the detection analysis may be improved.

For example, the multi-factor detection logic can detect, based in part on the outlier detection of the aggregated intervals, conditions or "red flag" events that are indicative of patient dependency, addiction, billing abuse, or diversion. Such conditions or events may include, for example, whether the patient 20 receives treatment from multiple doctors 22; whether the patient 20 receives treatment from multiple pharmacies 24; whether the patient 20 visits multiple urgent care facilities to obtain prescriptions; whether the patient 20 visits an emergency room or walk-in clinic to receive a prescription, rather than one of the doctors 22; whether the patient 20 is doctor shopping or pharmacy shopping; whether the patient 20 has stolen a prescription pad; whether the patient 20 traveled a long distance to obtain or fill the prescription; whether the patient 20 is prescribed medication above any acceptable level of use; and whether the patient 20 is being treated with a high morphine equivalency without stabilizing (i.e., showing signs of tolerance, dependency, or addiction).

The multi-factor detection logic may also detect conditions or "red flag" events that may be specific to a particular doctor 22, and may be indicative of doctor or provider billing abuse or diversion. Such conditions or events may include, for example, whether the doctor 22 provides the same or a different diagnosis with the same treatment patterns or medications; whether the doctor 22 prescribes medications having a high morphine equivalency for a majority or an uncharacteristically large number of patients 20; whether the drug intake of the patients stabilizes (i.e., the patients develop a tolerance or resistance to the medication) with no second ramp up (see, e.g., FIG. 7—weeks 12-26); whether the doctor 22 dispenses narcotics from the office, rather than writes a prescription to be filled by a pharmacy 24; whether the doctor 22 routinely dispenses narcotics from the office; and whether the doctor 22 is trading insurance information for narcotic prescriptions.

The multi-factor detection logic can also detect conditions or "red flag" events that may be specific to a particular pharmacy 24, and may be indicative of pharmacy billing abuse or diversion. Such conditions or events may include, for example, whether the pharmacy 24 bills a quantity less than was prescribed; whether pharmacy 24 submits a bill for the correct medication, but for a higher quantity than was actually dispensed; whether the pharmacy 24 dispenses additional refills to generate additional dispensing fees; whether the pharmacy 24 submits multiple bills for the same prescription; and whether the pharmacy 24 generates phantom bills to cover medications sold out the back door (i.e., drug diversion).

When the multi-factor detection logic 124 has identified a possible instance of improper drug use, an alert 48 is generated, as discussed above with regard to FIG. 2, and the outlier file 122 may be transmitted, at box 126, to an investigative services and/or audit department 50 of the insurance company 12. The investigative services and/or audit department 50 may conduct a review of the outlier file 122 and may take any necessary follow-up actions, such as those discussed above with regard to FIG. 2.

It should be appreciated that the model 100 shown in FIG. 11 allows for an analysis of medical billing data, and, in particular, the prescription drug regimen 60 of the patient 20, based on a standardization of the functional effect (i.e., morphine equivalency) of the medication to a common metric. For example, the standardization of the functional effect of the prescription drug regimen 60 enables more meaningful analysis of the medical billing data based on aggregate usage of a type of medication (i.e., narcotics), rather than for specific medications individually (i.e., methadone); and based on the duration of usage of the type of medication, rather than on specific medications, individually. The standardization of the functional effect of the prescription drug regimen 60 also enables the model 100 to identify doctors 22 who prescribe large amounts of narcotics or more frequently prescribe narcotics relative to a peer group, in general, rather than for specific medications, and/or pharmacies 24 that issue large amounts of narcotics or irregularly distribute narcotics relative to a peer group of pharmacies, as well as the usage by local patients and the issuance of prescriptions by local doctors.

Figure 12:
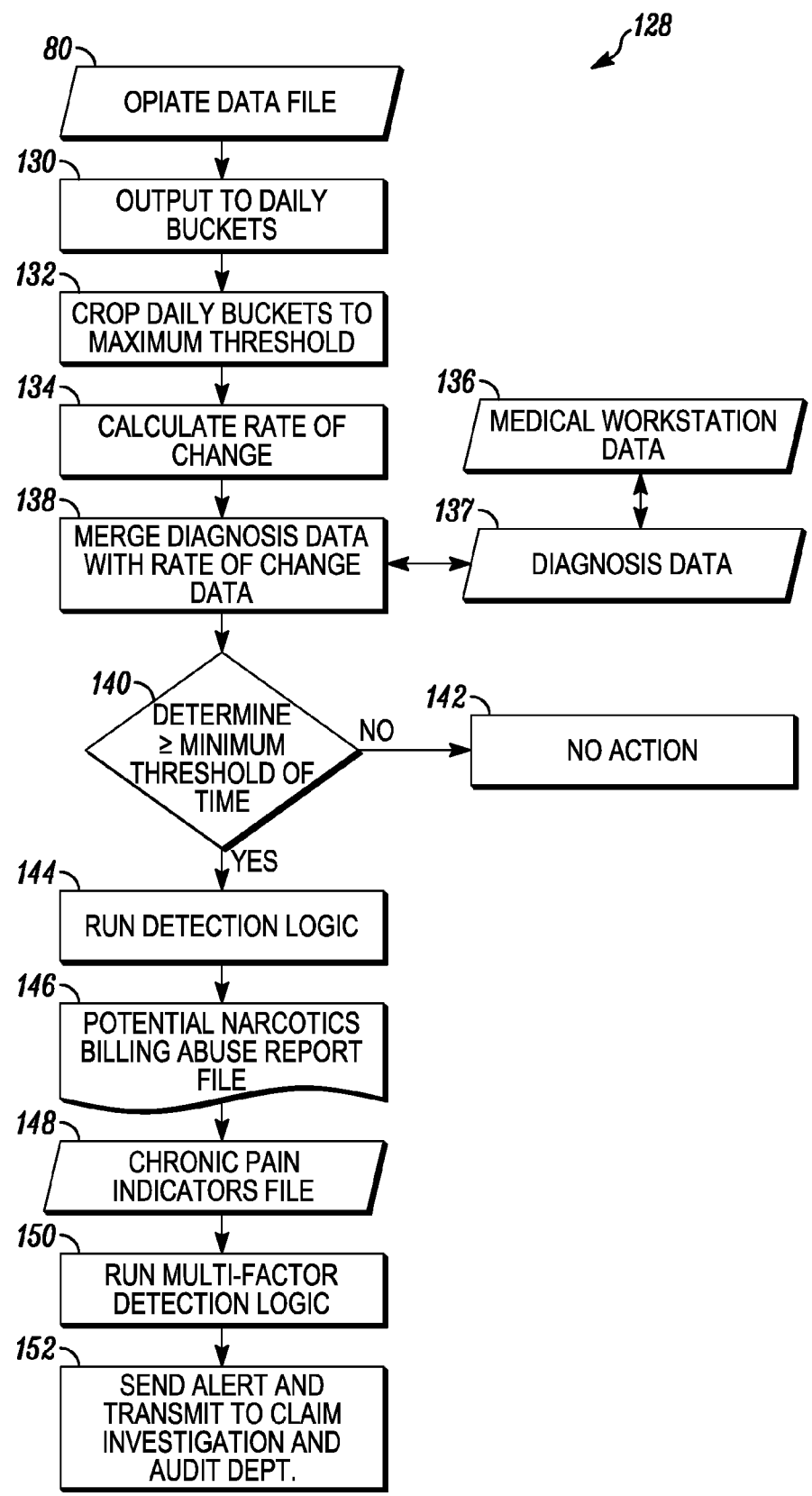
FIG. 12 is a flow diagram of a rate of change analysis model of the system and method according to an embodiment of the present invention.

Referring now to FIG. 12, a flow chart for a rate of change of morphine equivalency analysis model 128 based on an opiate data file 80 is shown. At box 130, the opiate data file 80 is first outputted into daily buckets of a calendar. The daily buckets may summarize the morphine equivalencies of a prescription drug regimen 60 of a patient 20 for each day.

At box 132, the daily buckets are then cropped to exclude daily buckets outside of a maximum threshold of time, such as after the first 180 days of treatment.

At box 134, the rate of change of the morphine equivalency of the prescription drug regimen 60 from one daily bucket to the next is calculated for the remaining (i.e., cropped) period of time. The rate of change data may be calculated, for example, using Equation 2, as discussed above. In addition, an average daily rate of change for the period of time may be calculated for a short-term interval, such as 14- or 30-days using Equation 2, as discussed above.

At box 138, diagnosis data 137 derived from medical workstation data 136 may be merged into the daily buckets, including the rate of change data, to determine a peer group.

Next, at box 140, it is determined whether the patient 20 has been on a prescription drug regimen 60 for more than a minimum threshold of time, such as 30-days of treatment. If the patient 20 does not have a treatment history that extends beyond the minimum threshold of time, then no further action is taken (box 142).

However, if the patient 20 has been on the prescription drug regimen 60 for more than the minimum threshold of time, then a detection logic 144 is run. For example, the detection logic 144 can be an outlier detection algorithm that compares the daily buckets of the patient, including the rate of change data and the average rate of change data for the short-term interval, to the daily buckets of the peer group for each respective day period of time.

After running the detection logic 144, a potential narcotics billing abuse report file 146 may be generated. The potential narcotics billing abuse report file 146 may be outputted as a chronic pain indicators file 148.

Next, a multi-factor detection logic is run at box 150 using the chronic pain indicators file 148 in conjunction with other detection logic and data sets based on a patient view, a doctor view and a pharmacist view, which, together, produce synergistic detection effects, as discussed above with regard to the detection logic 114 shown in FIG. 11.

In addition, a multi-factor detection analysis performed using the chronic pain indicators file 148 can also detect additional conditions or "red flag" events according to the three views, including, for example, whether the doctor 22 is distributing drugs improperly (i.e., diversion); whether the pharmacy 24 is distributing drugs improperly (i.e., diversion); and whether the patient 20 is developing a dependency or addiction to the prescription drug regimen 60.

Although these additional conditions can be detected using the outlier file 122 described in the model 100 of FIG. 11, performing a rate of change of morphine equivalency analysis using the rate of change data contained in the chronic pain indicators file 148 may detect these conditions or events in a different manner based on predicted patterns or trends, such as early signs of a ramp-up, a failure to stabilize, and a failure to change. The increased sensitivity of a multi-factor detection analysis based on the rate of change data contained in the chronic pain indicators file 148 increases the range at which the conditions are detected. The rate of change of morphine equivalency analysis model 128 shown in FIG. 12, which can identify the same types of dependency, addiction, billing abuse, and detection as the aggregation analysis model 100 shown in FIG. 11, may be used to identify dependency and/or addiction, since the chronic pain indicators file 148 identifies rapid and irregular increases (and decreases) in drug use, which is a precursor of dependency or addiction. In addition, running the multi-factor detection logic on the chronic pain indicators file 148 also improves the identification of abuse and/or diversion by identifying patterns that fail to exhibit naturally-shaped curvatures (i.e., which have a continuous, fixed ramp up or a fixed plateau of usage).

When the multi-factor detection logic 150 has identified a possible instance of improper drug use, an alert 48 is generated, as discussed above with regard to FIG. 2, and the chronic pain indicators file 148 may be transmitted to an investigative services and/or audit department 50 of the insurance company 12 at box 152. The investigative services and/or audit department 50 may conduct a review of the chronic pain identifiers file 148 and the potential narcotics abuse report file 146, and may take any necessary follow-up actions, such as those discussed above with regard to FIG. 2.

It should be appreciated that the rate of change of morphine equivalency analysis model 128 may enable the medical billing data, and, in particular, the prescription drug regimen 60 of the patient 20, to be analyzed based on a standardization of the change or "ramp up" in functional effect (i.e., morphine equivalency) of the medication to a common metric. For example, the standardization of the functional effect of the prescription drug regimen 60 enables a more meaningful, sensitive, and responsive analysis of the medical billing data and can detect indications of drug fraud and abuse, based on changes in use of medication by the patient 20, changes in issuances of prescriptions by the doctor 22, and changes in distribution of medication by the pharmacy 24. The detection may occur earlier in time relative to the injury of the patient and in response to different indicators relative to the aggregate use approach of model 100. The ability to detect early indications of change may enable preemptive action to be taken by the patient 20, the doctor 22, the pharmacy 24, employees of the insurance company, such as a claim investigator, a claim handler, a billing specialist, a member of another department, and the relevant authorities. As a result, the patient may be provided with better treatment, and the identified improper drug use may be responded to, thereby mitigating potential harms to the patient associated with the formation of a drug dependency or addiction; costs associated with claim payouts for instances of drug fraud and abuse; and risks to the public health, in general, associated with drug diversion into the black market.

In one embodiment of the present invention, one of the aggregate morphine equivalency analysis model 100 and the rate of change of morphine equivalency analysis model 128 are utilized to detect drug fraud and/or drug abuse. The model that is utilized may be selected by an employee of the insurance company 12, such as an employee from the billing department 36, claim department 38, the investigative services/audit department 50, or other department. According to this embodiment, if the model that has been selected indicates a possible instance of improper drug use, an alert 48 is generated, as discussed above with regard to FIGS. 11 and 12.

In another embodiment, both the aggregate morphine equivalency analysis model 100 and the rate of change of morphine equivalency analysis model 128 are utilized to detect drug fraud and/or drug abuse. According to this embodiment, if at least one of the models indicates a possible instance of improper drug use, an alert 48 is generated, as discussed above with regard to FIGS. 11 and 12.

Figure 13:
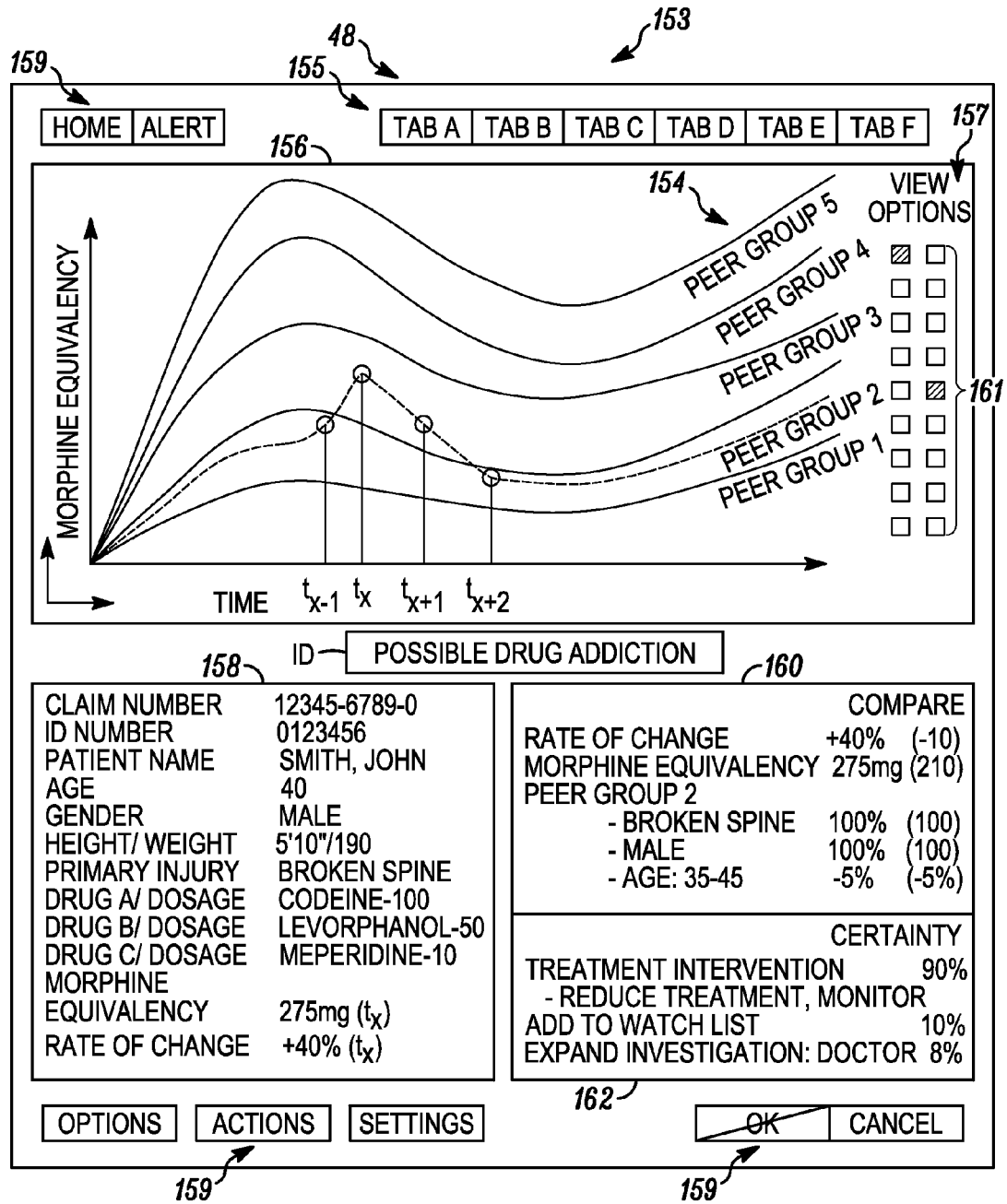
FIG. 13 depicts an example user interface according to an embodiment of the present invention.

Referring now to FIG. 13, an example user interface according to one embodiment of the present invention displaying an alert 48 is shown. The alert 48 may be displayed on any form of computer display, including a display associated with a desktop computer, a portable computer, a smart phone or a personal digital assistant ("PDA").

In particular, the alert 48 may be a dynamic alert user interface 153 or display, or a device with a display or user interface that may interact or exchange data with another entity, such as the claim handling system of an insurance company 12 (FIG. 1), for example. In one embodiment, the dynamic alert display 153 may be produced within a web-enabled portal, such as a browser, having a fully inter-operable architecture. As is shown in FIG. 13, the dynamic alert 153 reports an identified instance of potential drug fraud and/or drug abuse specific to the patient 20, the doctor 22, and/or the pharmacy 24, in the context of a relevant peer group (or groups) 154. For example, in FIG. 13, the alert identifier ("ID") indicates "POSSIBLE DRUG ADDICTION." The ID may be modified accordingly to indicate the nature of the drug fraud or drug abuse under review (e.g., drug diversion, billing fraud, etc.).

The dynamic alert 153 shown in FIG. 13 includes a dynamic graphical display 156, a dynamic alphanumeric data display panel 158, a dynamic prioritization of pertinent data display panel 160, and a dynamic prioritization of follow-up action data display panel 162.

The dynamic display 156 may enable a user, such as an employee in the investigative services and/or audit department 50, for example, to interact with the data in meaningful ways and to leverage all available data and graphing utilities to contextualize the content. In the illustrated embodiment, the dynamic display 156 includes a number of tabs 157, view options, and interaction buttons 159 that facilitate the importing or exporting of data and the control of the display settings. The tabs 157 (i.e., Tabs A-F) enable the user to easily transition between preset claim data views or windows. As an example, Tab A may be a fraud-alert window that sets forth the most relevant data specific to an identified instance of possible fraud (as shown in FIG. 13); Tab B may be a claim and billing history window (not shown); Tab C may be a patient medical history window (not shown); Tab D may be an administrative information window (not shown); Tab E may be a policy language and information window (not shown); and Tab F may be a chronological record of entries and edits to the patients' file history (not shown). Each Tab may be associated with a different data set that may be displayed graphically in the dynamic display 156.

The view options 157 (e.g., hot keys) in the illustrated embodiment may enable the user to easily manipulate the data presented in the dynamic display 156. For example, the view options 157 may include buttons 161 for showing or hiding data elements; showing or hiding a legend with raw data underlying the data elements that are shown; adjusting the time period of data displayed; correlating multiple data elements to a common metric; showing or hiding trend lines; adjusting opacity and layering of data elements; saving, loading or deleting the currently displayed view; and/or performing other display-related functions.

The interaction buttons 159 in the illustrated embodiment may enable the user to interact with the dynamic alert 153 in additional and more involved ways. For example, the "Options," "Actions" and "Settings" buttons 159 may provide access to less frequently utilized features of the claim handling system of the insurance company 12. Such features may include tools or utilities for importing, exporting, or interacting with raw data (e.g., to feed into another program); adjusting the configuration and/or settings of the claim handling window; submitting requests for the coding of new common view windows; reporting bugs; and/or performing other similar functions.

According to another embodiment, the "Options" button, for example, may be used to select the alert display 153 associated with a given analysis model 100, 128. For example, in the case where both the aggregate morphine equivalency analysis model 100 and the rate of change of morphine equivalency analysis model 128 are utilized, there is the potential for two possible instances of improper drug use (i.e., detections) and corresponding alerts 48 to be generated. The "Options" button (or other button) in that case may allow a user to view the respective displays 153, alternatively (i.e., as a toggle function) or simultaneously (e.g., in side-by-side windows).

to detect drug fraud and/or drug abuse. According to this embodiment, if at least one of the models indicates a possible instance of improper drug use, an alert 48 is generated, as discussed above with regard to FIGS. 11 and 12.

The dynamic alphanumeric data panel 158 in the illustrated embodiment may enable the investigative user to interact with the data directly, thereby facilitating the review, verification, and updating of such data.

The pertinent data display panel 160 may identify which factors or groupings of factors resulted in the positive identification of the possible instance of drug fraud or drug abuse (i.e., a general explanation of why the patient 20, the doctor 22 or the pharmacy 24 was flagged). The pertinent data display panel 160 may allow the user to more easily review the identified instance(s) of possible fraud and/or abuse. In addition, the user may interact with the pertinent data display panel 160, for example, to decrease the weighting or fully deactivate a specific pattern of fraud or abuse (i.e., if it has been eliminated as a possibility) or to increase the emphasis of another factor (i.e., if it has proven to be suspect).

The follow-up action display panel 162 may identify one or more possible courses of action to take as a follow-up to the dynamic alert 152 to mitigate the potential fraud or abuse situation. For example, in the illustrated embodiment the follow-up action display panel 162 lists numerous possible courses of action to take following the review by the investigative services and/or audit department 50 and includes weighting factors based on the data of the alert 48 and any adjustments and/or modifications that may be made by the investigative services and/or audit department 50. As a result, the archival knowledge of the insurance company 12 may be retained within the method and system of the present invention in a systematic and integrated manner.

For the exemplary insurance claim data that is shown in FIG. 13, the method of the present invention may issue the dynamic alert 153 at time ($t_x$). The dynamic alert 153 may indicate that the patient was exhibiting indications of a developing drug addiction at an earlier time (i.e., as of time $t_{x-1}$). In the illustrated embodiment, the follow-up action panel 162 of the dynamic alert 153 indicates that the best course of action is to intervene in the medical treatment of the patient by reducing the pharmaceutical drug regimen and monitoring the patient more closely. Pursuing this course of action may include contacting the patient and/or the doctor and recommending an adjustment to the prescription drug regimen of the patient.

The follow-up action panel 162 may also include precise details regarding when or how to intervene (e.g., as a matter of magnitude of change in treatment, using which techniques or alternative drug treatments and/or for what period of time). The details may be shown graphically on the dynamic display 156 and/or in alphanumeric text, which may appear at-length by floating or hovering the cursor or mouse over a given line of the follow-up action display panel 162. For example, the follow-up action panel 162 may indicate that intervention may be started immediately at a lower dosage of methadone (e.g., using the morphine equivalency standardization) for a period of two weeks (e.g., until time ($t_{x+2}$)). At the end of the two-week period, the patient's condition may be reevaluated and subsequent treatment decisions may be made to ensure that the patient's treatment pattern continues to substantially mirror the treatment patterns of his or her peer group.

According to an alternative embodiment, the systems and methods of the present invention may be applied to other categories of medications based on other standardized equivalencies, such as steroids, antibiotics, vasodilators or vasoconstrictors, beta blockers, diuretics, antihistamines, psychoactive drugs nicotine, and/or alcohol. In these non-narcotics fields, the risk of dependency or addiction may not pose as significant health risks to the patient, but the potential to improve health outcomes, reduce costs, and protect public health is equally present. The present invention may be used for application to other categories of medications that are highly addictive and/or subject to illegal trafficking. The present invention may also be used in the context of detoxification regimens, which can require careful balancing of the primary and cross-effects of the various medications, foods, and other substances to achieve the desired result.

According to an alternative embodiment of the present invention, the multi-factor detection logic may be based, in part, on data collected by health care billing or worker's compensation claim submissions or other data source.

According to an alternative embodiment of the present invention, the ICD codes may be truncated or further delineated to establish like-kind peer groups of sufficient size to have statistically significant figures. For example, ICD codes are typically formatted as "###.##" where the first three digits before the decimal indicate a primary or large grouping, and the two digits after the decimal indicate additional details about the specific condition. As an initial step to develop sufficiently large peer groups, the ICD codes can be truncated to the first three-digits. The amount of truncation and grouping, or conversely, further delineations of peer groups, is dependent upon the available data set. For optimal results, the ICD codes may be truncated or further delineated based on substantive and/or statistically significant similarities between truncated groupings or delineated subdivisions. For example, the application of medical knowledge may illuminate that a full break of a tibia may have similar pain and healing characteristics to a hairline fracture of a femur.

According to another embodiment of the present invention, the peer groups may be formed based on the use of multiple weighted diagnosis indicators. For example, a patient with a badly broken arm and a slightly fractured leg can be compared to a first peer group, whereas a patient with a slightly fractured arm and a badly broken leg can be compared to a second peer group, each peer group being distinct from the peer groups for broken or fractured arms and legs. The additional peer groups can be either distinctly defined and maintained (e.g., for the example above, the first and second peer groups can be separately stored in a database) or calculated using mathematical models that simulate the relative impact of a combination of injuries on a simulated peer group (e.g., for the example above, the first and second peer groups can rely upon peer groups for broken arms and broken legs that are merged using weighting equations).

According to another embodiment of the present invention, the detection logic and the data sets used in the multi-factor detection logic may include information concerning like-kind patient, doctor, and pharmacy groupings; doctor specialties; geographic norms, such as provider and pharmacy prevalence (i.e., relative density and/or scarcity); state-based availability or prohibitions regarding certain medications; patient medical histories or other available medical data. In addition, detection logic and the data sets used in the multi-factor detection analysis may be weighted to rely more or less heavily upon other attributes of the patient (e.g., patient demographic information, such as gender, age, height, weight, genetic markers, or indicators of drug metabolism rate, as well as the cross-effect of other medications or other disorders and diseases, comorbidity factors, etc.) to further stratify, separate, or aggregate the peer groups.

According to another embodiment of the present invention, the calculation of the rate of change may use another basic rate of change algorithm or a weighted rate of change algorithm, as follows:

$$ROC_B = (Amount_T - Amount_{T-1})/(Amount_T), \text{ or}$$

$$ROC_W = (Amount_T - Amount_{T-1})/(Amount_T + Amount_{T-1}),$$

Equation 3:

where $ROC_B$ and $ROC_W$ are basic and weighted rates of change, respectively, and where $Amount_T$ and $Amount_{T-1}$ are equivalencies determined at time T and time T−1, respectively.

According to another embodiment of the present invention, the calculation of the morphine equivalency of the prescription drug regimen may include a more sophisticated morphine equivalency equation based on, in part, the cross-effect of combinations of medications, including non-narcotics, and the cross-effect of other injuries sustained by the patient (i.e., a chronic organ condition, such as kidney failure, or an autoimmune disease) and other comorbidity issues.

According to another embodiment of the present invention, the various time periods (e.g., the minimum threshold of time, the maximum threshold of time, the moderate-term interval and the short-term interval) can be set to different lengths of time. For example, the minimum threshold of time may be set to approximately 30 days for a number of reasons, including where a statistically significant share of patients uses a prescription drug regimen with narcotics for less than 30 days; where the potential for the diagnosis to change during the first 30 days exists; and where there is an insufficient history to analyze treatment in shorter time increments. However, the minimum threshold of time could be reduced if the data and analysis justify a more responsive start period. Since the step of determining whether the patient has been on a prescription drug regimen for more than the minimum threshold of time usually occurs after data is gathered and sorted into aggregated intervals or daily buckets, the necessary information regarding the appropriateness of a minimum threshold of time will be available to feed back into the model to determine how to set the minimum threshold of time.

Similarly, the maximum threshold of time may be set to approximately 180 days for a number of reasons, including where a dwindling patient population is continuously on the prescription drug regimen beyond 180 days; where a reduced likelihood of drug dependency or addiction forming after such a lengthy exposure to the prescription drug regimen is observed or expected; where a reduced volatility of the amount of morphine equivalency of the prescription drug regimen as a successful amount is determined earlier in treatment; and where the cost exposure, and, thus, the incentive to monitor such cases, is decreased. However, the maximum time threshold could be increased if the data and analysis justify a more protracted end period.

The moderate-time interval may be set to approximately 30 days for a number of reasons, including where it is desired for the moderate-term interval to include two or more prescription cycles that are often at least seven-days in length. However, the moderate-term interval can be increased, decreased, or circumstantially adjusted, for example, on a per-injury basis, if the data and analysis justify a different period of time.

The short-term interval may be set to approximately 14 days for a number of reasons, including where it is desired for the short-term interval to include two or more prescription cycles that are often at least seven-days in length. However, the short-term interval can be increased, decreased, or circumstantially adjusted, for example, on a per-injury basis, if the data and analysis justify a different period of time.

It should also be appreciated that the system and method of the present invention may be adapted to collect and store data that has been inputted or generated, in order to expand the working data set. The constant feed of new data may enable the system and method of the present invention to utilize increasingly defined peer groups having greater specialization of information based on a further stratification of ailments and injuries, patient demographics, doctor specializations, differentiating characteristics of pharmacies, available medications and treatments, and respective timing considerations regarding the same.

According to another embodiment of the present invention, the system and method of the present invention may also be used in applications outside of the insurance context. For example, the outputs of the present invention may be entered into a medical diagnostic and treatment system and method, such as a software package that is configured to operate on a computer and, in particular, a desktop computer, a portable computer, a smart phone or a PDA. A provider or pharmacist can then utilize the medical diagnostic and treatment system and method to more accurately prescribe treatment options for the patient to reduce the incidence of drug abuse.

As another example, the method and system of the present invention may be applied as a screening tool to evaluate an individual's health and/or inclination to commit fraud. For example, it is a common practice in some industries (e.g., government, military, law enforcement, pharmaceutical companies, hospitals, and pharmacies) to screen new employees, job applicants, or other individuals for drug use. Beyond the immediate concerns associated with a person who is using various drugs, the screening may also be conducted to identify individuals with a greater propensity to become a drug addict or to commit fraud in the future. The method and system of the present invention can be utilized to identify individuals with a propensity to become addicted and to commit fraud based on their prior medical records and accumulated data regarding associated peer groups.

As another example, the method and system of the present invention, through its ordinary use, gathers data regarding the fraud and abuse propensity of the patient, the doctor, and the pharmacy populations. This data, and, in particular, as outputted using the dynamic alert of the present invention, may be leveraged to supplement genetic testing and research, public health education, and socio-informatics, in general. For example, this data may identify patient populations with increased propensities to develop an addiction to a drug, such as a narcotic, which can be published and disseminated to alert the relevant populations to the relative risks that they face.

As another example, the method and system of the present invention may have additional utility in other legal contexts. In particular, the method and system of the present invention may provide information that may prove relevant in the context of a litigation matter, for example, to substantiate the mental or physical capacity of an individual who committed a tort under the influence of a number of substances (e.g., a drunk or heavily medicated driver). In addition, the method and system of the present invention may be used by customs agents to review drug traffic in a more meaningful manner by leveraging the standardized pharmaceutical effect of substances transported across a border in the aggregate and with respect to a rate of change thereof.

In another embodiment of the present invention, the method and system of the present invention may be implemented using electronic transaction records (e.g., credit and debit card purchases, electronic bank transfers, or other transactions that can be tracked or stored electronically, or electronic inventory information of suppliers) as a source of data for determining drug usage, in place of or in addition to the medical billing records.

It should be understood that the foregoing description is only illustrative of the present invention. Various alternatives and modifications can be devised by those skilled in the art without departing from the broader aspects of the present invention.

What is claimed is:

1. A computer-implemented method for detecting an improper drug use, comprising:
    determining, by at least one processing device, morphine equivalency data for each drug of a plurality of drugs of a drug regimen of a patient, and for each time period of a plurality of time periods;
    determining, by the at least one processing device, a total morphine equivalency for the drug regimen for each time period of the plurality of time periods, wherein the total morphine equivalency for the drug regimen for each time period comprises a sum of the morphine equivalency data for each drug of the plurality of drugs of the drug regimen of the patient for each respective time period;
    identifying, by the at least one processing device, a possible instance of the improper drug use associated with the drug regimen based on the morphine equivalency data, using the at least one processor, wherein the identifying comprises determining that the total morphine equivalency for the drug regimen for at least one of the time periods of the plurality of time periods is outside of an expected range compared to a total morphine equivalency for a comparable time period of a peer group associated with the drug regimen;
    generating, by the at least one processing device, an alert for the possible instance of the improper drug use; and
    causing, by the at least one processing device, an outputting of an indication of the alert.

2. The method of claim 1, wherein the improper drug use comprises at least one of a drug fraud and a drug abuse.

3. The method of claim 1, wherein the peer group associated with the drug regimen comprises one or more of a peer group of doctors and a peer group of pharmacies.

4. The method of claim 1, wherein the peer group associated with the drug regimen comprises a peer group of patients having at least one of (i) the same injury as the patient, (ii) the same disease classification code as the patient, and (iii) the same partial disease classification code as the patient.

5. The method of claim 1, further comprising displaying at least a portion of the total morphine equivalency on at least one computer display.

6. The method of claim 5, further comprising displaying a plot of the total morphine equivalency over the plurality of time periods.

7. The method of claim 1, further comprising transmitting the alert to at least one of an insurance company entity, a doctor, a pharmacy, and an authority.

8. The method of claim 3, wherein the peer group associated with the drug regimen comprises a peer group of doctors, and the peer group of doctors comprises one or more of (i) doctors having a similar specialty to a doctor associated with the drug regimen and (ii) doctors that have treated patients similar to the patient associated with the drug regimen.

9. The method of claim 1, further comprising determining a treatment plan for the patient based on the total morphine equivalency.

10. The method of claim 1, further comprising causing a display of a comparison of the total morphine equivalency for the drug regimen of the patient to the total morphine equivalency of the peer group associated with the drug regimen on a computer display.

11. The method of claim 1, wherein the morphine equivalency data comprises rate of change data for a predetermined period of time.

12. The method of claim 3, wherein the peer group associated with the drug regimen comprises a peer group of pharmacies, and the peer group of pharmacies comprises pharmacies that have fulfilled a similar volume of prescriptions as a pharmacy associated with a prescription of the drug regimen to the patient.

13. The method of claim 1, wherein the morphine equivalency data comprises duration of use data.

14. A system, comprising:
a processing device; and
a memory device in communication with the processing device, the memory device storing instructions that when executed by the processing device result in:
determining morphine equivalency data for each drug of a plurality of drugs of a drug regimen of a patient, and for each time period of a plurality of time periods;
determining a total morphine equivalency for the drug regimen for each time period of the plurality of time periods, wherein the total morphine equivalency for the drug regimen for each time period comprises a sum of the morphine equivalency data for each drug of the plurality of drugs of the drug regimen of the patient for each respective time period;
identifying a possible instance of the improper drug use associated with the drug regimen based on the morphine equivalency data, wherein the identifying comprises determining that the total morphine equivalency for the drug regimen for at least one of the time periods of the plurality of time periods is outside of an expected range compared to a total morphine equivalency for a comparable time period of a peer group associated with the drug regimen;
generating an alert for the possible instance of the improper drug use; and
causing an outputting of an indication of the alert.

15. The system of claim 14, wherein the improper drug use comprises at least one of a drug fraud and a drug abuse.

16. The system of claim 14, wherein the peer group associated with the drug regimen comprises one or more of a peer group of doctors and a peer group of pharmacies.

17. The system of claim 16, wherein the peer group associated with the drug regimen comprises a peer group of doctors, and the peer group of doctors comprises one or more of (i) doctors having a similar specialty to a doctor associated with the drug regimen and (ii) doctors that have treated patients similar to the patient associated with the drug regimen.

18. The system of claim 16, wherein the peer group associated with the drug regimen comprises a peer group of pharmacies, and the peer group of pharmacies comprises pharmacies that have fulfilled a similar volume of prescriptions as a pharmacy associated with a prescription of the drug regimen to the patient.

19. The system of claim 14, wherein the peer group associated with the drug regimen comprises a peer group of patients having at least one of (i) the same injury as the patient, (ii) the same disease classification code as the patient, and (iii) the same partial disease classification code as the patient.

20. The system of claim 14, wherein the instructions, when executed by the processing device, further result in:
transmitting the alert to at least one of an insurance company entity, a doctor, a pharmacy, and an authority.

21. The system of claim 14, wherein the instructions, when executed by the processing device, further result in:
determining a treatment plan for the patient based on the total morphine equivalency.

22. The system of claim 14, wherein the morphine equivalency data comprises rate of change data for a predetermined period of time.

23. A non-transitory computer-readable medium storing instructions that when executed by a processing device result in:
determining morphine equivalency data for each drug of a plurality of drugs of a drug regimen of a patient, and for each time period of a plurality of time periods;
determining a total morphine equivalency for the drug regimen for each time period of the plurality of time periods, wherein the total morphine equivalency for the drug regimen for each time period comprises a sum of the morphine equivalency data for each drug of the plurality of drugs of the drug regimen of the patient for each respective time period;
identifying a possible instance of the improper drug use associated with the drug regimen based on the morphine equivalency data, wherein the identifying comprises determining that the total morphine equivalency for the drug regimen for at least one of the time periods of the plurality of time periods is outside of an expected range compared to a total morphine equivalency for a comparable time period of a peer group associated with the drug regimen;
generating an alert for the possible instance of the improper drug use; and
causing an outputting of an indication of the alert.

24. The non-transitory computer-readable medium of claim 23, wherein the improper drug use comprises at least one of a drug fraud and a drug abuse.

25. The non-transitory computer-readable medium of claim 23, wherein the peer group associated with the drug regimen comprises one or more of a peer group of doctors and a peer group of pharmacies.

26. The non-transitory computer-readable medium of claim 25, wherein the peer group associated with the drug regimen comprises a peer group of doctors, and the peer group of doctors comprises one or more of (i) doctors having a similar specialty to a doctor associated with the drug regimen and (ii) doctors that have treated patients similar to the patient associated with the drug regimen.

27. The non-transitory computer-readable medium of claim 25, wherein the peer group associated with the drug regimen comprises a peer group of pharmacies, and the peer group of pharmacies comprises pharmacies that have fulfilled a similar volume of prescriptions as a pharmacy associated with a prescription of the drug regimen to the patient.

28. The non-transitory computer-readable medium of claim 23, wherein the peer group associated with the drug regimen comprises a peer group of patients having at least one of (i) the same injury as the patient, (ii) the same disease classification code as the patient, and (iii) the same partial disease classification code as the patient.

29. The non-transitory computer-readable medium of claim 23, wherein the instructions, when executed by the processing device, further result in:
   transmitting the alert to at least one of an insurance company entity, a doctor, a pharmacy, and an authority.

30. The non-transitory computer-readable medium of claim 23, wherein the instructions, when executed by the processing device, further result in:
   determining a treatment plan for the patient based on the total morphine equivalency.

31. The non-transitory computer-readable medium of claim 23, wherein the morphine equivalency data comprises rate of change data for a predetermined period of time.

* * * * *